United States Patent
Chen et al.

(10) Patent No.: US 11,312,715 B2
(45) Date of Patent: Apr. 26, 2022

(54) FUSED RING DERIVATIVE AS $A_{2A}$ RECEPTOR INHIBITOR

(71) Applicants: CSTONE PHARMACEUTICALS (SUZHOU) CO., LTD., Jiangsu (CN); CSTONE PHARMACEUTICALS (SHANGHAI) CO., LTD., Shanghai (CN); CSTONE PHARMACEUTICALS, Grand Cayman (KY)

(72) Inventors: Kevin X Chen, Shanghai (CN); Kai Zhou, Shanghai (CN); Boyu Hu, Shanghai (CN); Minliang Xiao, Shanghai (CN); Shuhui Chen, Shanghai (CN)

(73) Assignees: CSTONE PHARMACEUTICALS (SUZHOU) CO., LTD., Suzhou (CN); CSTONE PHARMACEUTICALS (SHANGHAI) CO., LTD., Shanghai (CN); CSTONE PHARMACEUTICALS, Grand Cayman (KY)

( * ) Notice: Subject to any disclaimer, the term of this patent is extended or adjusted under 35 U.S.C. 154(b) by 43 days.

(21) Appl. No.: 16/650,967

(22) PCT Filed: Sep. 27, 2018

(86) PCT No.: PCT/CN2018/107899
§ 371 (c)(1),
(2) Date: Mar. 26, 2020

(87) PCT Pub. No.: WO2019/062803
PCT Pub. Date: Apr. 4, 2019

(65) Prior Publication Data
US 2020/0239465 A1    Jul. 30, 2020

(30) Foreign Application Priority Data

Sep. 28, 2017  (CN) .......................... 201710900542.8
Mar. 21, 2018  (CN) .......................... 201810239824.2

(51) Int. Cl.
*C07D 471/04*  (2006.01)
*C07D 519/00*  (2006.01)
*A61P 35/00*  (2006.01)

(52) U.S. Cl.
CPC ............ *C07D 471/04* (2013.01); *A61P 35/00* (2018.01); *C07D 519/00* (2013.01)

(58) Field of Classification Search
CPC .......................... C07D 471/04; C07D 519/00
USPC ....................................................... 514/249
See application file for complete search history.

(56) References Cited

U.S. PATENT DOCUMENTS

| | | | |
|---|---|---|---|
| 5,922,725 A | 7/1999 | Teuber et al. | |
| 6,222,035 B1 | 4/2001 | Tsumuki et al. | |
| 7,317,007 B2 | 1/2008 | Alanine et al. | |
| 7,855,202 B2 | 12/2010 | Vidal Juan et al. | |
| 10,407,424 B2 * | 9/2019 | Chan .................. | A61K 31/444 |
| 2004/0006082 A1 | 1/2004 | Harada et al. | |
| 2009/0023763 A1 | 1/2009 | Vidal Juan et al. | |
| 2015/0252041 A1 | 9/2015 | Jonczyk et al. | |

FOREIGN PATENT DOCUMENTS

| | | |
|---|---|---|
| CN | 1437471 A | 8/2003 |
| CN | 105025899 A | 11/2015 |
| JP | 2007532603 A | 11/2007 |
| JP | 2009510152 A | 3/2009 |
| JP | 201531381 A | 2/2015 |
| RU | 2136676 C1 | 9/1999 |
| WO | WO-2005095360 A1 | 10/2005 |
| WO | WO-2005100353 A1 | 10/2005 |
| WO | WO-2008031875 A1 | 3/2008 |
| WO | WO-2014101373 A1 | 7/2014 |
| WO | WO-2015020565 A1 | 2/2015 |

(Continued)

OTHER PUBLICATIONS

Russian Office Action issued in Russian Patent Application No. 2020114314, dated Dec. 14, 2020.
Korean Office Action issued in Korean Patent Application No. 10-2020-7012498, dated Dec. 18, 2020.
Sep. 24, 2020 Japanese Office Action issued in Japanese Patent Application No. 2018-506472.
Aug. 20, 2020 Korean Office Action issued in Korean Patent Application No. 1020170126922.
First Mexican Office Action for corresponding Application No. MX/a/2020/0037320 dated Feb. 16, 2021.
Extended European Search Report regarding EP 18861150.3, dated Mar. 4, 2021.

(Continued)

*Primary Examiner* — Niloofar Rahmani
(74) *Attorney, Agent, or Firm* — Harness, Dickey & Pierce, P.L.C.

(57) ABSTRACT

Disclosed are a compound represented by formula (I) or a pharmaceutically acceptable salt thereof, and an application of the compound or slat in preparation of drugs for treating diseases related to an $A_{2A}$ receptor.

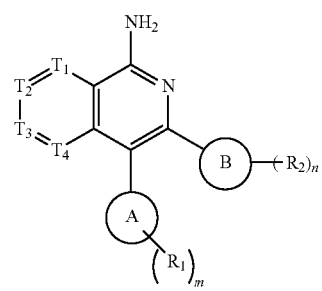

(I)

18 Claims, No Drawings

(56) References Cited

FOREIGN PATENT DOCUMENTS

WO    WO-2015031221 A1    3/2015
WO    WO-2018183956 A1 * 10/2018  ............. A61K 45/06

OTHER PUBLICATIONS

Indian Office Action issued in Indian Patent Application No. 202047016826, dated Apr. 27, 2021.

Jan. 4, 2019 International Search Report issued in International Patent Application No. PCT/CN2018/107899.

Jan. 4, 2019 Written Opinion of the International Searching Authority issued in International Patent Application No. PCT/CN2018/107899.

* cited by examiner

FUSED RING DERIVATIVE AS $A_{2A}$ RECEPTOR INHIBITOR

CROSS-REFERENCE TO RELATED APPLICATIONS

This application is a 371 National Phase of International Application No. PCT/CN2018/107899, filed Sep. 27, 2018, which claims the benefit of Chinese Patent Application No. CN 201710900542.8, filed Sep. 28, 2017 and Chinese Patent Application No. CN 201810239824.2, filed Mar. 21, 2018. The entire disclosures of the above applications are incorporated herein by reference.

FIELD OF THE INVENTION

The present disclosure relates to a compound represented by formula (I) or a pharmaceutically acceptable salt thereof, and a use thereof in the manufacture of a medicament for treating a disease related to an $A_{2A}$ receptor.

PRIOR ARTS

Adenosine $A_{2A}$ receptor is widely distributed in human tissues and highly expressed in tissues and organs such as spleen, thymus, white blood cells, blood platelets, GABA-type neurons and olfactory bulb. It is also expressed in other parts such as heart, lung, blood vessels and brain. Adenosine $A_{2A}$ receptor generally co-exists with other GPCR and they binds together to form heterodimers, for example, $A_{2A}$ receptor can form heterodimers with dopamine $D_2$, cannabinoid $CB_1$, glutamic acid mGluR5, etc. Adenosine $A_{2A}$ receptor plays an important role in regulating vasodilation, supporting the formation of new blood vessels and protecting body tissues from injury caused by inflammation; adenosine $A_{2A}$ receptor also affects the activity of indirect basal ganglia pathway.

In solid tumors, the decomposition of cellular tissues and anoxic environment cause a large amount of ATP decomposition, thus leading to extracellular adenosine enrichment to an abnormally high concentration, which is 10-20 times of normal value. The high concentration of adenosines bind to $A_{2A}$ receptor, thereby activating the adenosine signaling pathway. This signal pathway is a mechanism that protects the body tissue through immunosuppression when the body tissue is damaged. Activation of the adenosine signaling pathway leads to long-term inhibition of innate immune response, which will produce immune tolerance and leads to uncontrolled growth of malignant tumors. The binding of adenosine to $A_{2A}$ receptor in white blood cells (e.g., lymphocytes, T lymphocytes, natural killer cells, dendritic cells, etc.) inhibits the effector function of these white blood cells in the immune system. The binding of adenosine to $A_{2A}$ receptor increases the expression of CD39, CD73 and CTLA4 (T cell checkpoint), thereby producing more $T_{reg}$ cells with stronger immunosuppression. Blocking the adenosine signaling pathway of $A_{2A}$ receptor can reduce the inhibitory effect on immune system and enhance the immune function of T cells, thus it is considered to be a promising negative feedback mechanism that can inhibit tumor growth.

Monoclonal antibody CS1003 is a full-length, fully humanized immunoglobulin G4 (IgG4) monoclonal antibody for PD-1.

Content of the Invention

The present disclosure provides a compound represented by formula (I) or a pharmaceutically acceptable salt thereof,

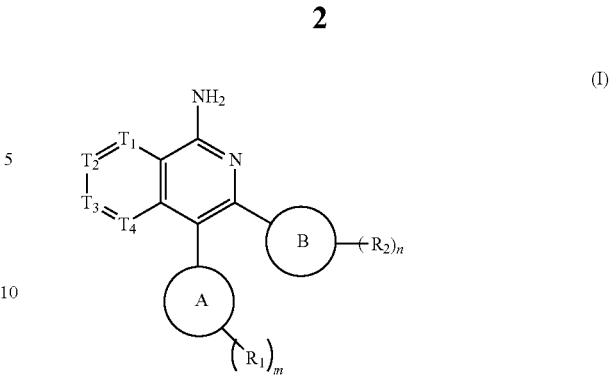

wherein,
1 or 2 of $T_1$, $T_2$, $T_3$ and $T_4$ is N, the rest are independently CH;
each of $R_1$ is independently selected from H, halogen, OH, $NH_2$ or $C_{1-3}$ alkyl optionally substituted by 1, 2 or 3 R;
each of $R_2$ is independently selected from H, halogen, OH, $NH_2$ or $C_{1-3}$ alkyl optionally substituted by 1, 2 or 3 R;
n is selected from 0, 1, 2 and 3;
m is selected from 0, 1, 2 and 3;
ring A is selected from 6-10 membered aryl and 5-10 membered heteroaryl;
ring B is selected from phenyl and 5-6 membered heteroaryl;
R is selected from F, Cl, Br, I, OH, $NH_2$ and CN;
the "hetero" in the 5-6 membered heteroaryl and 5-10 membered heteroaryl are each independently selected from N, O, S, NH, —C(=O)—, —C(=O)O— and —C(=O)NH—;
the number of the heteroatom or heteroatom group is independently selected from 1, 2, 3 and 4.

In some embodiments of the present disclosure, each of $R_1$ is independently selected from H, F, Cl, Br, I, OH, $NH_2$, Me and Et, wherein the Me and Et are optionally substituted by 1, 2 or 3 R, other variants are as defined in the present disclosure.

In some embodiments of the present disclosure, each of $R_1$ is independently selected from H, F, Cl, Br, I, OH, $NH_2$, Me, $CF_3$ and Et, other variants are as defined in the present disclosure.

In some embodiments of the present disclosure, each of $R_2$ is independently selected from H, F, Cl, Br, I, OH, $NH_2$ and Me optionally substituted by 1, 2 or 3 R, other variants are as defined in the present disclosure.

In some embodiments of the present disclosure, each of $R_2$ is independently selected from F, Cl, Br, I, OH, $NH_2$ and Me, other variants are as defined in the present disclosure.

In some embodiments of the present disclosure, ring A is selected from phenyl, pyridyl, quinolyl, quinoxalyl, 1,2,3,4-tetrahydroquinolyl, 3,4-dihydro-2H-benzo[b][1,4]oxazinyl, [1,2,4]triazolo[1,5-a]pyridyl, 1H-indazolyl, benzo[d]isoxazolyl, triazolo[4,3-a]pyridyl and 1H-benzo[d][1,2,3]triazolyl, other variants are as defined in the present disclosure.

In some embodiments of the present disclosure, ring A is selected from phenyl, pyridyl, quinolyl, quinoxalyl, 1,2,3,4-tetrahydroquinolyl, 3,4-dihydro-2H-benzo[b][1,4]oxazinyl, [1,2,4]triazolo[1,5-a]pyridyl, 1H-indazolyl, benzo[d]isoxazolyl, triazolo[4,3-a]pyridyl, 1H-benzo[d][1,2,3]triazolyl, cinnolinyl, quinazolinyl, quinolyl, isoquinolyl, imidazo[1,2-a]pyridyl, [1,2,4]triazolo[1,5-a]pyridyl, 1H-indazolyl and benzo[d]thiazolyl, other variants are as defined in the present disclosure.

In some embodiments of the present disclosure, the structural unit
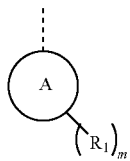
is selected from
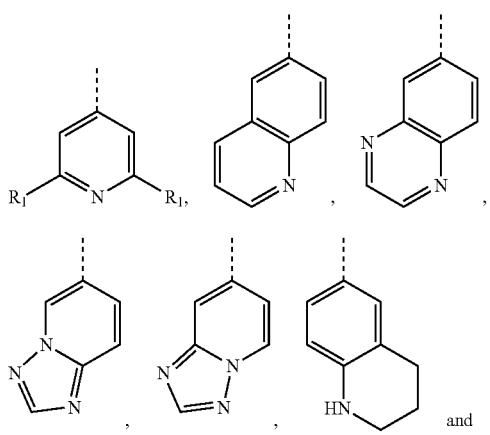
other variants are as defined in the present disclosure.
In some embodiments of the present disclosure, the structural unit
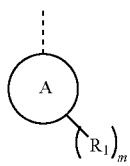
is selected from
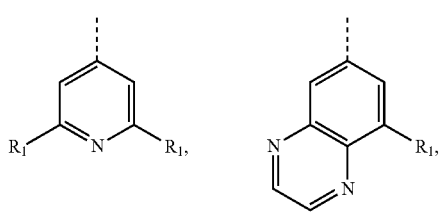
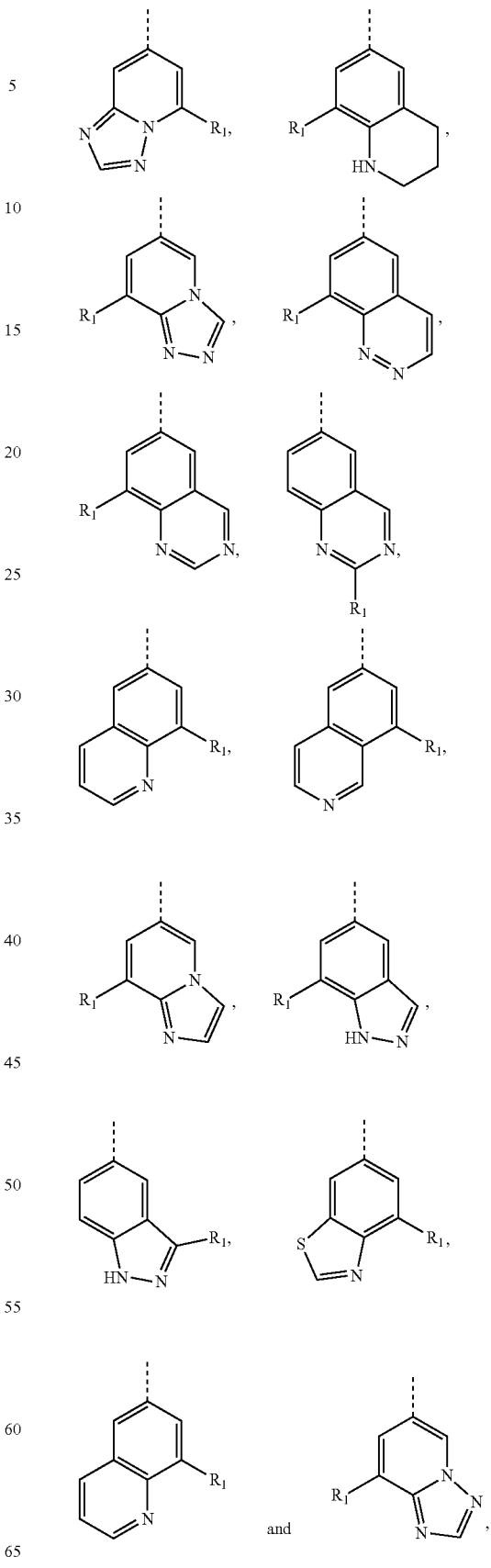
other variants are as defined in the present disclosure.

In some embodiments of the present disclosure, the structural unit

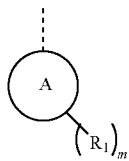

is selected from

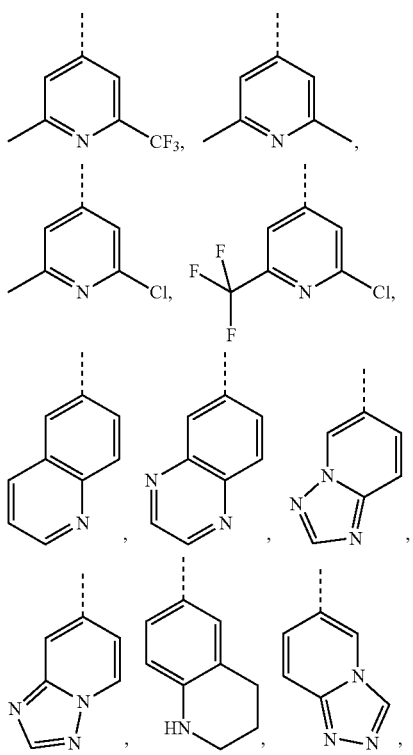

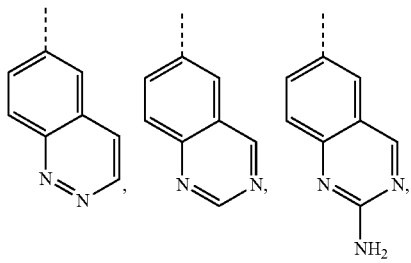

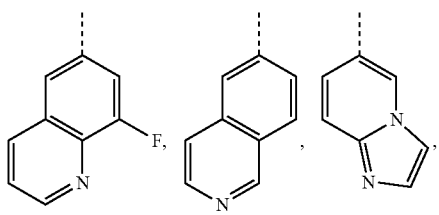

-continued

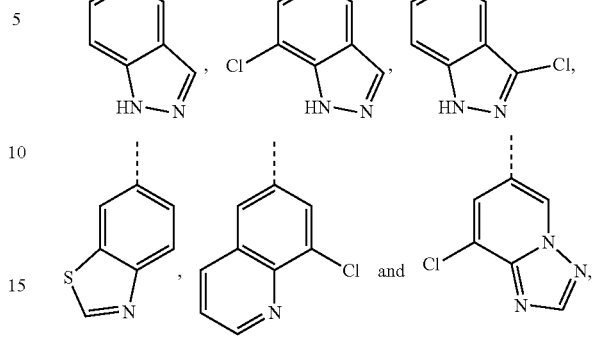

other variants are as defined in the present disclosure.

In some embodiments of the present disclosure, the structural unit

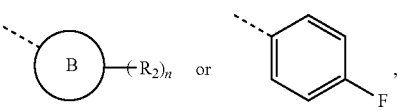 or 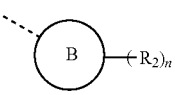

other variants are as defined in the present disclosure.

In some embodiments of the present disclosure, ring B is selected from phenyl, furanyl, thienyl and pyrazolyl, other variants are as defined in the present disclosure.

In some embodiments of the present disclosure, the structural unit

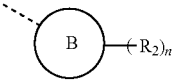

is selected from

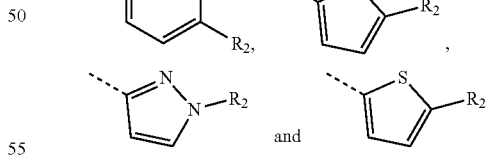

other variants are as defined in the present disclosure.

In some embodiments of the present disclosure, the structural unit is selected from

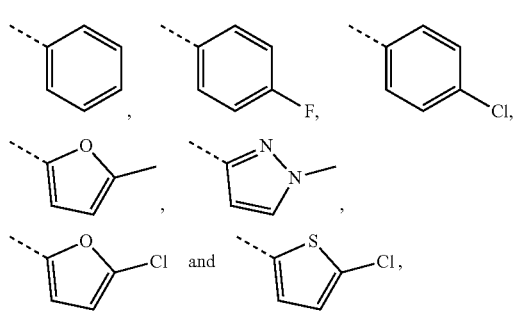

other variants are as defined in the present disclosure.

In some embodiments of the present disclosure, the structural unit

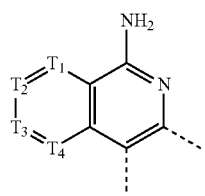

is selected from:

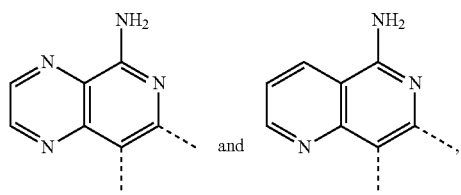

other variants are as defined in the present disclosure.

In some embodiments of the present disclosure, the structural unit

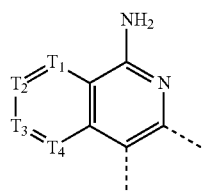

is selected from

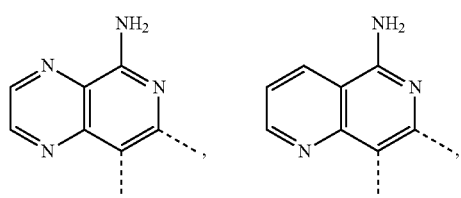

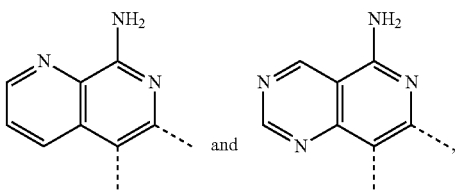

other variants are as defined in the present disclosure.

In some embodiments of the present disclosure, the compound or the pharmaceutically acceptable salt thereof is selected from

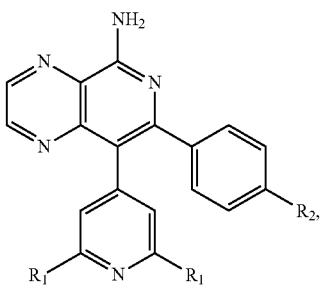

(I-1)

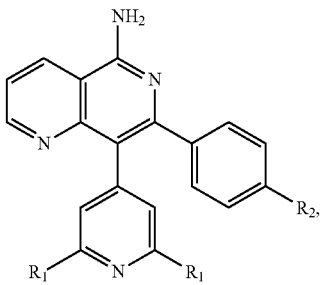

(I-2)

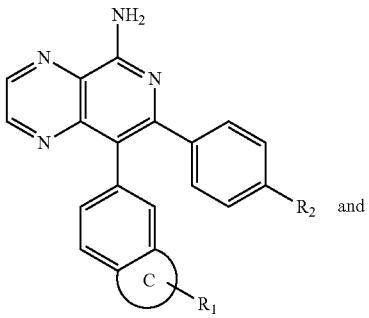

(I-3) and

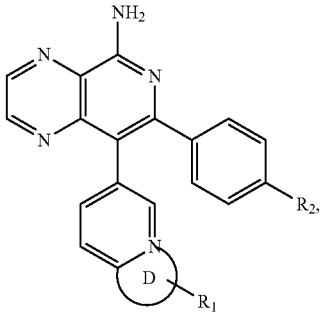

(I-4)

wherein,

R₁ and R₂ are as defined in the present disclosure;

ring C is selected from 5-6 membered heteroaryl and 5-6 membered heterocycloalkyl;

ring D is selected from 5-6 membered heteroaryl;

the "hetero" in the 5-6 membered heteroaryl is selected from N, S and NH;

the "hetero" in the 5-6 membered heterocycloalkyl is NH;

the number of the heteroatom or heteroatom group is independently selected from 1, 2, 3 and 4.

In some embodiments of the present disclosure, the structural unit

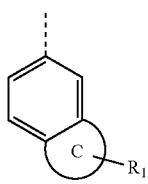

is selected from

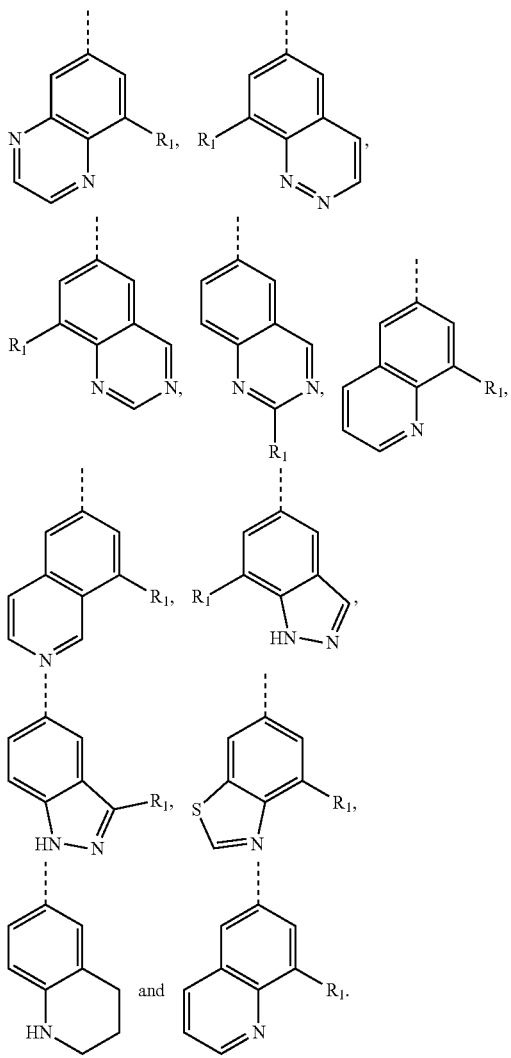

In some embodiments of the present disclosure, the structural unit

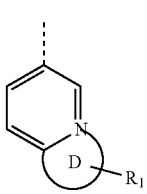

is selected from

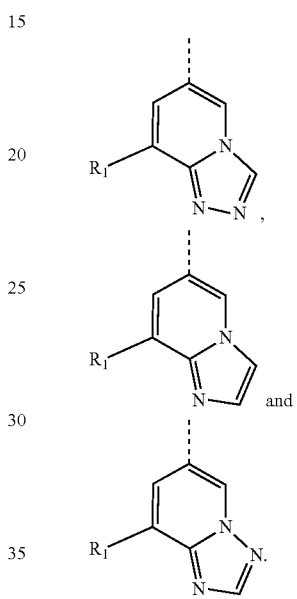

The other embodiments of the present disclosure are obtained by arbitrary combination of the above variants.

The present disclosure also provides a compound represented by the following formula or a pharmaceutically acceptable salt thereof:

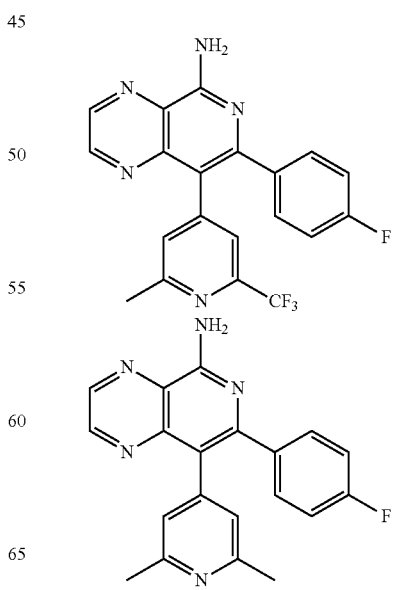

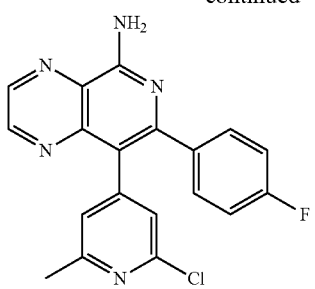
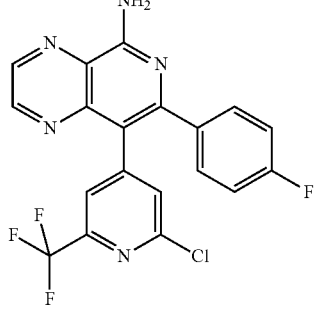
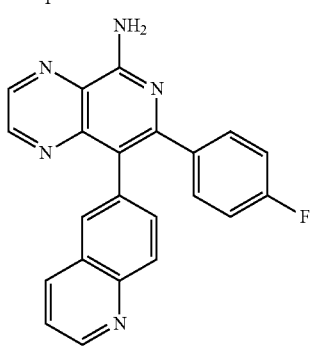
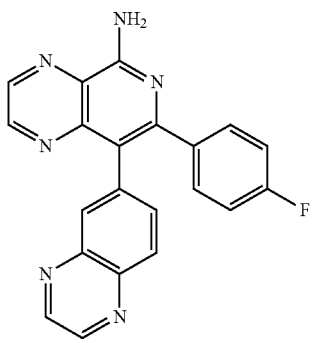
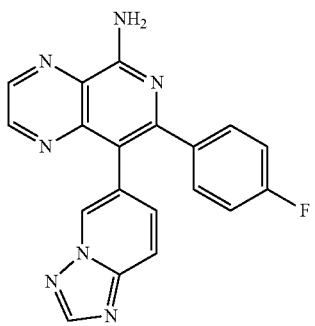
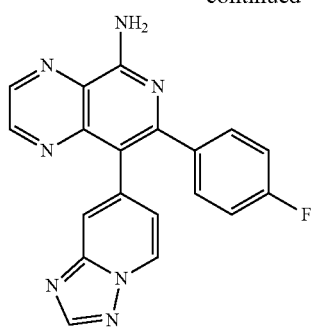
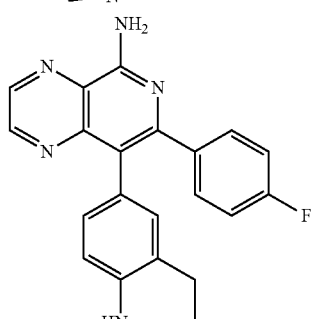
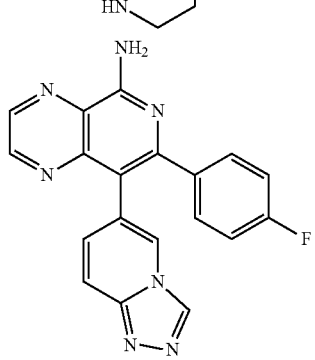
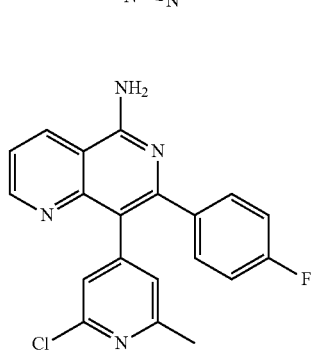
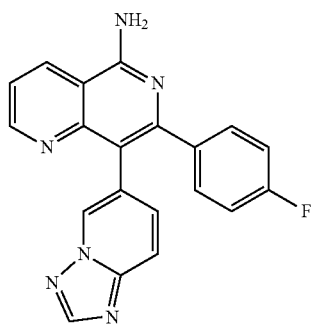

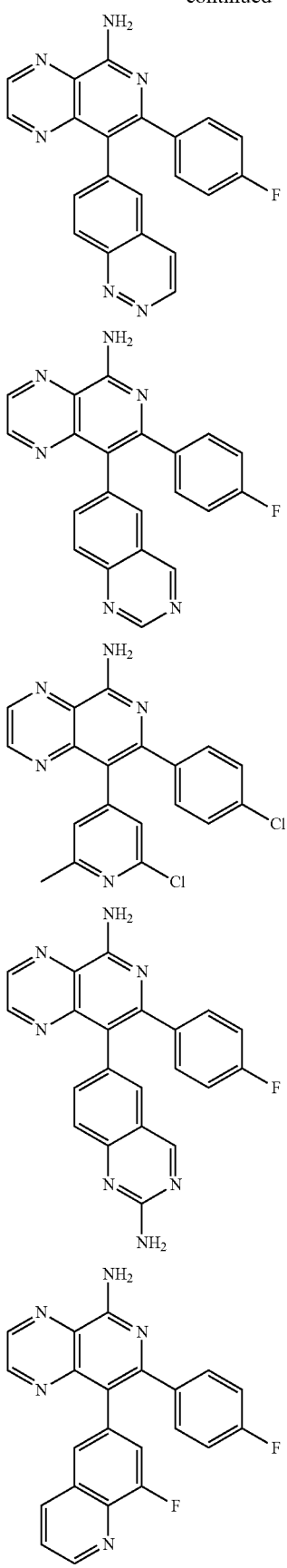
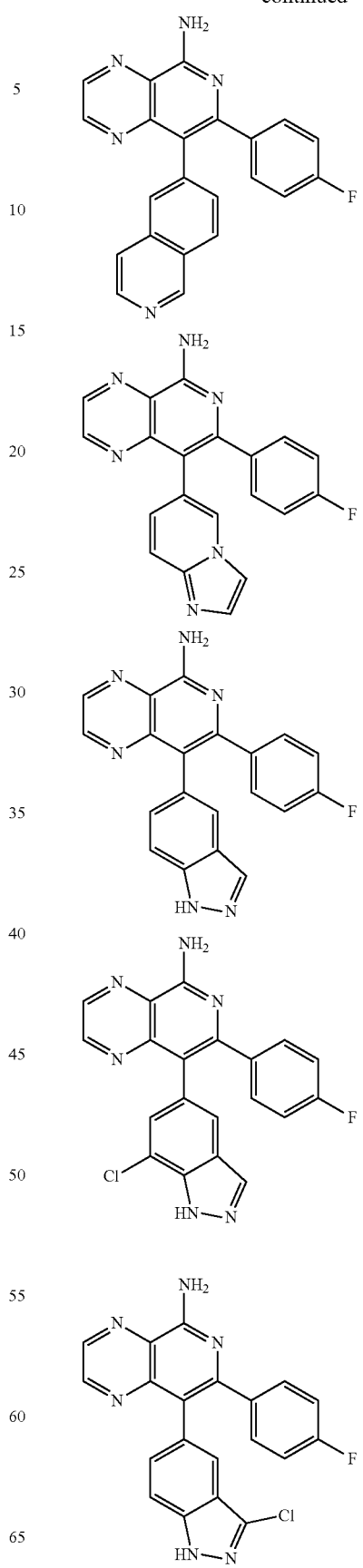

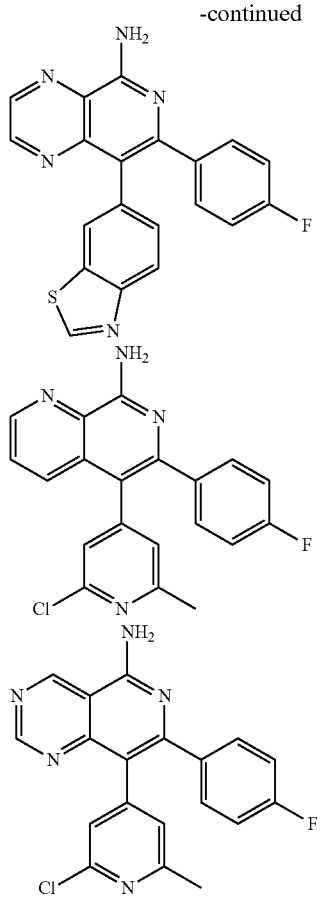
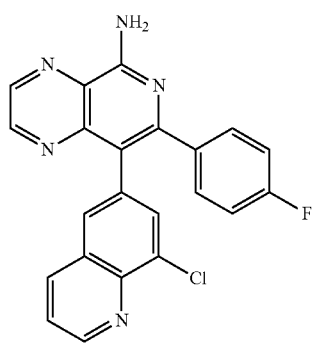
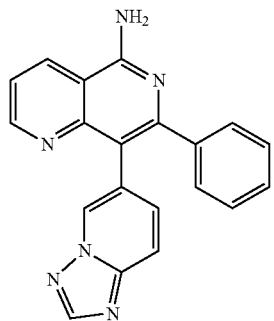
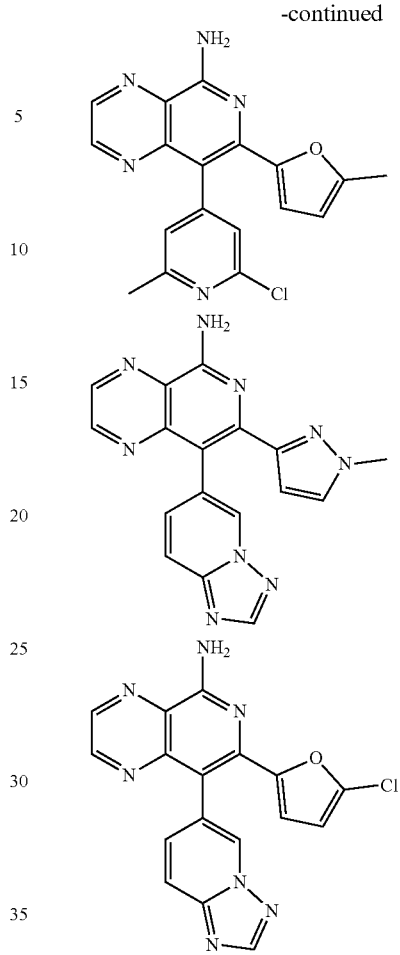
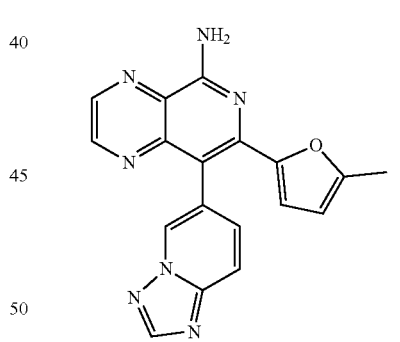
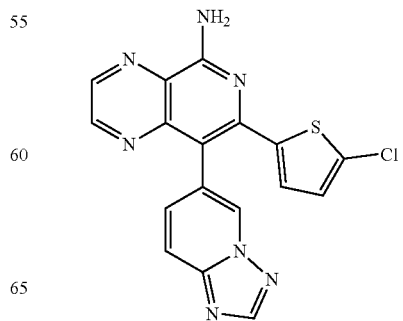

-continued

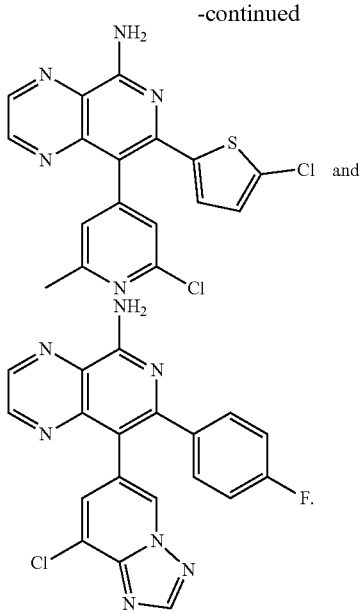

The present disclosure also provides application use of the compound or the pharmaceutically acceptable salt thereof in the manufacture of a medicament for treating a disease related to A2A receptor.

Technical Effect

The present application synthesizes a compound of formula (I) which is a new adenosine A2A antagonist. The compound can be used for tumor immunotherapy in single drug or in combination with an antibody. The compound of the present disclosure has better solubility and obviously improves the pharmacokinetic characteristics.

The combination of the compound of the present disclosure and CS1003 achieves a better tumor inhibition effect, and has a synergistic effect.

The compound of the present disclosure has sufficient exposure in plasma and tumor tissues.

Definition and Description

Unless otherwise indicated, the following terms when used in the descriptions and the claims of the present disclosure have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present disclosure that contain both basic and acidic functional groups can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

In addition to the salt form, the compound provided by the present disclosure also exists in prodrug form. The prodrug of the compound described herein is the compound that readily undergoes chemical change under physiological condition to be converted into the compound of the present disclosure. Additionally, the prodrug can be converted to the compound of the present disclosure by a chemical or biochemical method in vivo environment.

Certain compounds of the present disclosure can exist in a nonsolvated form or a solvated form, including hydrated form. Generally, the solvated form is equivalent to the nonsolvated form, and both are encompassed within the scope of the present disclosure.

The compound of the present disclosure may have a specific geometric or stereoisomeric form. The present disclosure contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present disclosure. The substituent such as alkyl may have an additional asymmetric carbon atom. All these isomers and mixtures thereof are encompassed within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability of a double bond or a single bond of carbon atoms on the ring to freely rotate.

Unless otherwise specified, the term "diastereomer" refers to stereoisomers in which the molecules have two or more chiral centers and are not mirror images of each other.

Unless otherwise specified, "(D)" or "(+)" refers to dextrorotation, "(L)" or "(−)" refers to levorotation, "(DL)" or "(±)" refers to racemization.

Unless otherwise specified, the absolute configuration of a stereogenic center is represented by a wedged solid bond ( ◢ ) and a wedged dashed bond ( ◌ ), and the relative configuration of a stereogenic center is represented by a straight solid bond ( ▬ ) and a straight dashed bond ( ┄ ). A wave line ( ∿ ) represents a wedged solid bond ( ◢ ) or a wedged dashed bond ( ◌ ), or represents a straight solid bond ( ▬ ) or a straight dashed bond ( ┄ ).

The compounds of the present disclosure may be present in particular. Unless otherwise indicated, the terms "tautomer" or "tautomeric form" refer to the fact that the different functional isomers are in dynamic equilibrium at room temperature and can be rapidly converted into each other. If tautomers are possible (e.g., in solution), the chemical equilibrium of the tautomers can be achieved. For example, proton tautomers (also known as prototropic tautomers) include interconversions by proton transfer, such as keto-enol isomerization and imine-enamine isomerization. The valence tautomer includes the mutual transformation of some bonding electrons. A specific example of keto-enol tautomerization is the interconversion between two tautomers of pentane-2,4-dione and 4-hydroxypent-3-en-2-one.

Unless otherwise specified, the terms "enriched in one isomer", "isomer enriched", "enriched in one enantiomer" or "enantiomer enriched" refer to the content of one of the isomers or enantiomers is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the terms "excess of isomer" or "excess of enantiomer" refers to the difference between the relative percentages of the two isomers or enantiomers. For example, wherein, the content of one of the isomers or enantiomers is 90%, and the other one is 10%, then the excess of isomer or enantiomer (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, hydrogen can be replaced by heavy hydrogen to form a deuterated drug, and the bond composed of barium and carbon is stronger than the bond composed of common hydrogen and carbon. Compared with undeuterated drugs, deuterated drugs have reduced side effects and increased drug stability, enhanced the efficacy and prolonged the biological half-life of the drug. All isotopic variations of the compound of the present disclosure, whether radioactive or not, are encompassed within the scope of the present disclosure. The term "pharmaceutically acceptable carrier" refers to any agent or carrier medium which is capable of delivering an effective amount of the active substance of the present disclosure, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field.

The term "excipient" generally refers to a carrier, a diluent and/or a medium required for formulating an effective pharmaceutical composition.

For a medicament or a pharmacologically active agent, the term "effective amount" or "therapeutically effective amount" refers to a nontoxic but sufficient amount to achieve a desired effect of the medicament or the agent. For the oral dosage form of the present disclosure, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled person in the art based on routine experiment.

The term "active ingredient", "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to more than one atom on a ring, such substituent can be bonded to any atom of the ring. For example, the structural unit

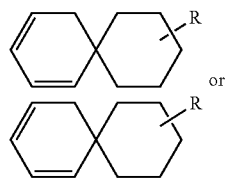

means that the substituent R can be located at any position on cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring. When the enumerative linking group does not indicate the direction for linking, the direction for linking is arbitrary, for example, the linking group L contained in

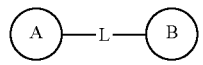

is -MW—, then -MW— can link ring A and ring B to form in

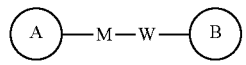

the direction same as left-to-right reading order, and form

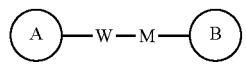

in the direction contrary to left-to-right reading order. A combination of substituents and/or variants thereof is allowed only when such combination can result in a stable compound.

Unless otherwise specified, the term "hetero" represents a heteroatom or a heteroatomic group (e.g., an atomic group containing a heteroatom), including the atom except carbon (C) and hydrogen (H) and the atomic group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a double ring, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclyl" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)$_p$, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzo-imidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1H-1,2,3-triazolyl, 2H-1,2,3-triazolyl, 1H-1,2,4-triazolyl, 4H-1,2,4-triazolyl and xanthenyl. Also included are fused-ring compounds and spiro compounds.

Unless otherwise specified, the term "hydrocarbyl" or its hyponyms (e.g., alkyl, alkenyl, alkynyl, and aryl, etc.), by itself or as part of another substituent, refers to a linear, branched chain or cyclic hydrocarbon radical or any combination thereof. They can be fully saturated (e.g., alkyl), mono- or polyunsaturated (e.g., alkenyl, alkynyl, and aryl), can be mono-, di- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two consecutive heteroatoms can be present, such as, —$CH_2$—NH—$OCH_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remainder position of the molecule. Examples of the cyclohydrocarbyl include, but are not limited to, cyclopentyl, cyclohexyl, 1-cyclohexenyl, 3-cyclohexenyl, cycloheptyl and the like. Non-limiting examples of heterocyclyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydrothiophen-3-yl, 1-piperazinyl and 2-piperazinyl.

Unless otherwise specified, the term "alkyl" refers to a linear chain or branched saturated hydrocarbon group, can be mono-substituted (e.g., —$CH_2F$) or poly-substituted (e.g., —$CF_3$), can be monovalent (e.g. methyl), divalent (e.g., methylene) or multivalent (e.g., methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl, benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "aralkyl" is meant to include the group (e.g., benzyl, phenethyl, pyridylmethyl, etc.) where an aryl is attached to an alkyl, including an alkyl where the carbon atom (e.g., methylene) has been replaced by an atom such as oxygen, for example, phenoxymethyl, 2-pyridyloxy, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present disclosure can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present disclosure.

All of the solvents used in the present disclosure are commercially available. The present disclosure adopts the abbreviating words as followed: "aq" refers to water; "HATU" refers to O-(7-azabenzotriazol-1-yl)-N,N,N',N'-tetramethyluronium hexafluorophosphate; "EDC" refers to N-(3-dimethylaminopropyl)-N'-ethylcarbodiimide hydrochloride; "m-CPBA" refers to 3-chloroperoxybenzoic acid; "eq" refers to equivalent; "CDI" refers to carbonyldiimidazole; "DCM" refers to dichloromethane; "PE" refers to petroleum ether; "DIAD" refers to diisopropyl azodicarboxylate; "DMF" refers to N,N-dimethylformamide; "DMSO" refers to dimethyl sulfoxide; "EtOAc" refers to ethyl acetate; "EtOH" refers to ethanol; "MeOH" refers to methanol; "CBz" refers to benzyloxycarbonyl, which is an amine protecting group; "BOC" refers to tert-butoxycarbonyl, which is an amine protecting group; "HOAc" refers to acetic acid; "NaCNBH$_3$" refers to sodium cyanoborohydride; "r.t." refers to room temperature; "O/N" refers to overnight; "THF" refers to tetrahydrofuran; "Boc$_2$O" refers to di-tert-butyldicarbonate; "TFA" refers to trifluoroacetic acid; "DIPEA" refers to diisopropylethylamine; "SOCl$_2$" refers to thionyl chloride; "CS$_2$" refers to carbon disulfide; "TsOH" refers top-toluenesulfonic acid; "NFSI" refers to N-fluoro-N-(phenylsulfonyl)benzenesulfonamide; "NCS" refers to 1-chloropyrrolidine-2,5-dione; "n-Bu$_4$NF" refers to tetrabutylammonium fluoride; "iPrOH" refers to 2-propanol; "mp" refers to melting point; "LDA" refers to diisopropylamino lithium; NBS refers to N-bromosuccinimide.

Compounds are named manually or by ChemDraw® software, the commercially available compounds use their vendor directory names.

The synthesis of the intermediates are as follows.

DETAILED DESCRIPTION OF THE PREFERRED EMBODIMENT

The following embodiments further illustrate the present disclosure, but the present disclosure is not limited thereto. The present disclosure has been described in detail herein, and specific embodiments thereof have also been disclosed. It will be apparent to those skilled in the art that various changes and modifications can be made to the specific embodiments of the present disclosure without departing from the spirit and scope of the present disclosure.

Synthesis of Intermediate 3C:

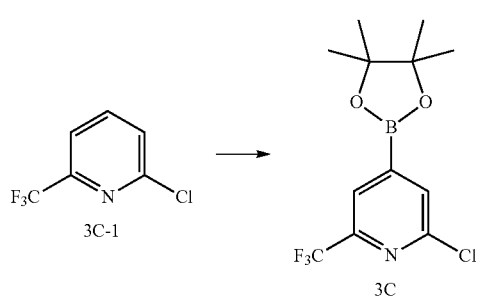 [SMILES: FC(F)(F)c1cccc(Cl)n1 ; CC1(C)OB(c2cc(Cl)nc(C(F)(F)F)c2)OC1(C)C]

The compound bis(pinacolato)diboron (25.61 g, 100.85 mmol, 0.65 eq), (1,5)-cyclooctadiene methoxy iridium dimer (308.56 mg, 465.48 μmol, 0.003 eq) and 4,4-di-tert-butyl-2,2-bipyridine (249.88 mg, 930.96 μmol, 0.006 eq) were dissolved in n-hexane (250 mL), and the reaction mixture was stirred at 50° C. under nitrogen protection until the reaction mixture turned dark red. Compound 3C-1 was added to the above solution, and then the reaction mixture was stirred for 3 hours at 50° C. under nitrogen protection. LCMS showed the complete conversion to the hydrolysis product of compound 3C borate. The reaction mixture was filtered and concentrated under reduced pressure to give the crude product of compound 3C, which was directly used in the next step without purification.

Relevant characterization data: LCMS m/z: 206.1 [M+H] (showing that the borate was hydrolyzed to boric acid).

$^1$H NMR (400 MHz, CDCl$_3$): δ 7.83 (s, 1H), 7.70 (s, 1H), 1.37 (s, 12H).

Synthesis of Intermediate 5E:

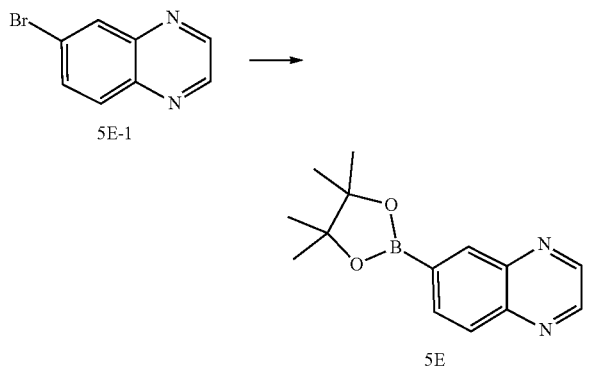

Compound 5E-1 (0.5 g, 2.39 mmol, 1 eq), bis(pinacolato)diboron (668.12 mg, 2.63 mmol, 1.1 eq), [1,1-bis(diphenylphosphino)ferrocene]palladium dichloride (II) (87.51 mg, 119.59 μmol, 0.05 eq), potassium acetate (352.11 mg, 3.59 mmol, 1.5 eq) were dissolved in 10 mL dioxane and reacted at 80° C. for 12 hours under nitrogen protection. LCMS showed the complete conversion to the product. The reaction mixture was filtered and concentrated under reduced pressure to give the crude product of compound 5E, which was directly used in the next step without purification.

Relevant characterization data: LCMS m/z: 257.2 [M+H].

$^1$H NMR (400 MHz, CDCl$_3$): δ 8.87 (d, J=4.8 Hz, 2H), 8.61 (s, 1H), 8.15 (dd, J=20.4, 8.4 Hz, 2H), 1.40 (s, 12H).

Synthesis of Intermediate 6F:

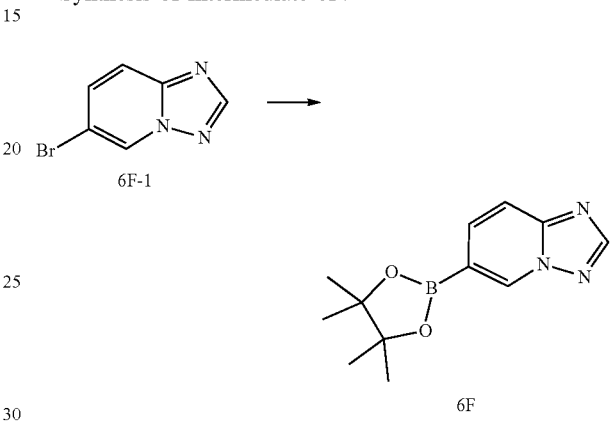

Compound 6F-1 (0.5 g, 2.39 mmol, 1 eq), bis(pinacolato)diboron (769.43 mg, 3.03 mmol, 1.2 eq), [1,1-bis(diphenylphosphino)ferrocene]palladium dichloride (II) (92.38 mg, 126.25 μmol, 0.05 eq), potassium acetate (743.43 mg, 7.57 mmol, 3 eq) were dissolved in 5 mL dioxane and reacted at 80° C. for 12 hours under nitrogen protection. LCMS showed the complete conversion to the product. The reaction mixture was filtered and concentrated under reduced pressure to give the crude product of compound 6F, which was directly used in the next step without purification.

Relevant characterization data: LCMS m/z: 246.1 [M+H]

$^1$H NMR (400 MHz, CDCl$_3$): δ 8.97 (s, 1H), 8.36 (s, 1H), 8.15 (dd, J=8.0, 23.6 Hz, 2H), 1.35 (s, 12H).

Synthesis of Intermediate 7G:

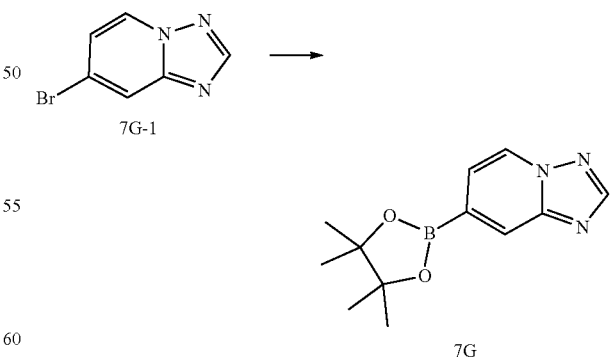

Compound 7G-1 (0.135 g, 681.75 μmol, 1 eq), bis(pinacolato)diboron (190.43 mg, 749.92 μmol, 1.1 eq), potassium acetate (100.36 mg, 1.02 mmol, 1.5 eq), tri(dibenzylideneacetone)dipalladium (31.21 mg, 34.09 μmol, 0.05 eq), PCy$_3$ (19.12 mg, 68.17 μmol, 22.10 μL, 0.1 eq) were dissolved in 2 mL dioxane and stirred at 80° C. for 12 hours under nitrogen protection. LCMS showed the complete conversion to the product. The reaction mixture was filtered and the filtrate was concentrated under reduced pressure to give a crude product of compound 7G, which was directly used in the next step without purification.

Relevant characterization data: LCMS m/z: 164.1 [M+H] (the MS of the hydrolysis product of compound 8H)

$^1$H NMR (400 MHz, CDCl$_3$): δ 8.59 (d, J=6.8 Hz, 1H), 8.39 (d, J=6.8 Hz, 1H), 7.62 (s, 1H), 8.36 (s, 1H), 1.40 (s, 12H).

Synthesis of Intermediate 8H:

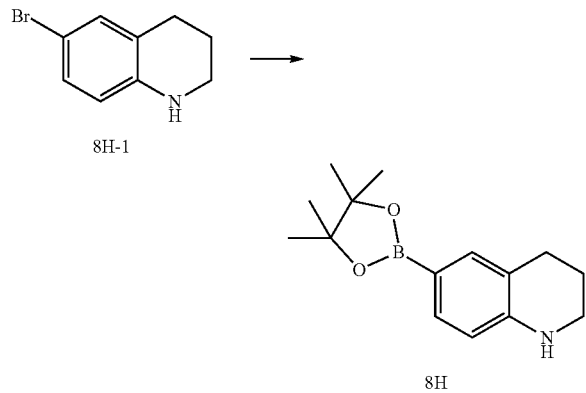

(1,1'-Bis(diphenylphosphino)ferrocene)palladium dichloride (II) (345.00 mg, 471.51 μmol, 0.2 eq), potassium acetate (694.12 mg, 7.07 mmol, 3.0 eq) and compound 8I1-1 (500 mg, 2.36 mmol, 1.0 eq) were added into a solution of bis(pinacolato)diboron (718.40 mg, 2.83 mmol, 1.2 eq) in 1,4-dioxane (3 mL), the mixture was heated to 90° C. under nitrogen protection and stirred for 10 hours. The mixture was filtered and concentrated, and purified by column chromatography (SiO$_2$, PE/ethyl acetate gradient elution, volume ratio from 20/1 to 10/1) to give compound 8I1.

Relevant characterization data: LCMS m/z: 260.1 [M+H].

Synthesis of Intermediate 9I:

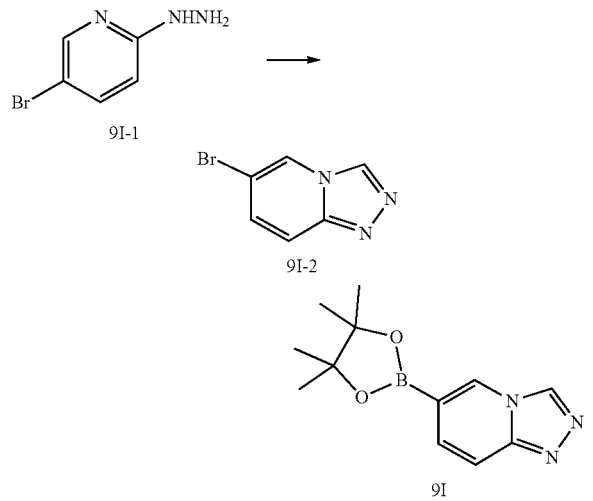

Step 1 (Synthesis of Compound 9I-2)

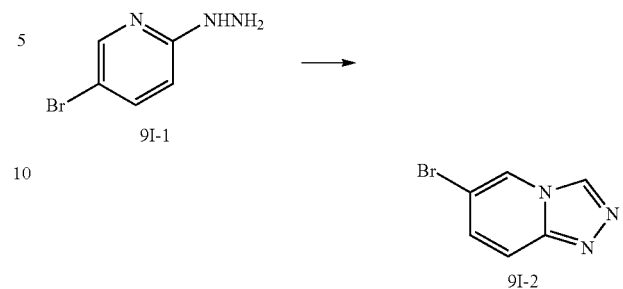

p-Toluenesulfonic acid (228.96 mg, 1.33 mmol, 0.05 eq) was added into a solution of compound 9I-1 (5 g, 26.59 mmol, 1 eq) in triethyl orthoformate (50 mL), and the reaction mixture was stirred at 110° C. for 12 hours. The reaction mixture was cooled to room temperature, concentrated and evaporated to dryness. The residue was diluted with water (50 mL), adjusted to pH=9 with saturated sodium bicarbonate solution, extracted with ethyl acetate. The organic phases were combined and washed with saturated brine (30 mL*2), dried over anhydrous sodium sulfate, filtered and evaporated to dryness. The crude product was separated and purified by column chromatography (PE/ethyl acetate gradient elution, volume ratio from 3/1 to pure ethyl acetate) to give compound 9I-2.

Relevant characterization data: LCMS m/z: 197.9 [M+H]

$^1$H NMR (400 MHz, CDCl$_3$): δ 8.80 (s, 1H), 8.32 (d, J=1.2 Hz, 1H), 7.73 (t, J=13.8 Hz, 1H), 7.35 (dd, J=1.6, 9.6 Hz, 1H).

Step 2 (Synthesis of Compound 9I)

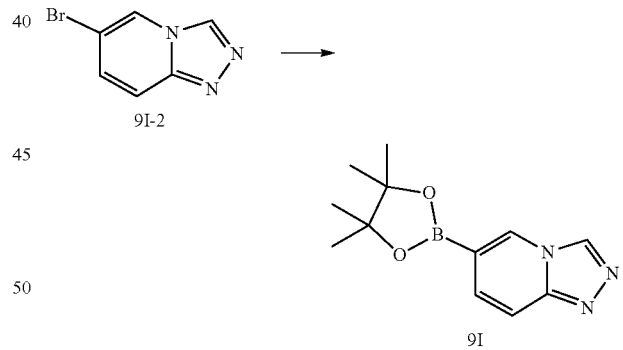

Under nitrogen protection, a solution of compound 9I-2 (0.5 g, 2.52 mmol, 1 eq), pinacol borate (705.31 mg, 2.78 mmol, 1.1 eq), Pd(dppf)$_2$Cl$_2$.CH$_2$Cl$_2$ (103.10 mg, 126.25 μmol, 0.05 eq) and potassium acetate (371.71 mg, 3.79 mmol, 1.5 eq) in dioxane (5 mL) was stirred at 80° C. for 12 hours. LCMS showed that the reaction was complete, then the reaction mixture was cooled to room temperature, filtered, and the filtrate was evaporated to dryness to give the crude product of compound 9I.

Relevant characterization data: LCMS m/z: 197.9 [M+H]

$^1$H NMR (400 MHz, CDCl$_3$): δ 8.81 (s, 1H), 8.53 (s, 1H), 7.75 (t, J=9.6 Hz, 1H), 7.58 (t, J=9.6 Hz, 1H), 1.37 (s, 12H).

Synthesis of Intermediate 13J:

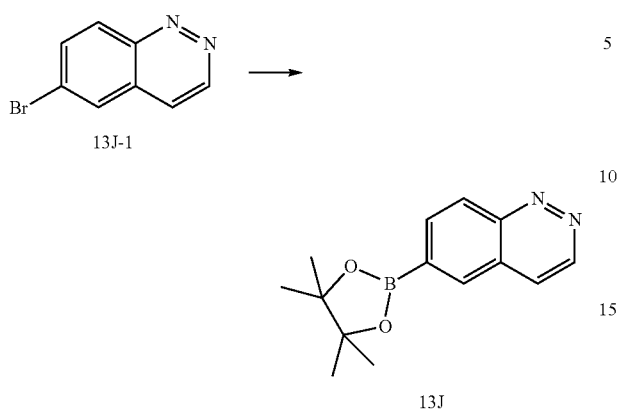

Compound 13J-1 (50 mg, 239.19 μmol, 1 eq), bis(pinacolato)diboron (66.81 mg, 263.10 μmol, 1.1 eq), potassium acetate (46.95 mg, 478.37 μmol, 2 eq) and Pd(dppf)$_2$Cl$_2$ (15.59 mg, 23.92 μmol, 0.1 eq) were added into 1,4-dioxane (2 mL). The mixture was heated to 80° C. under nitrogen protection and stirred at 80° C. for 10 hours. LC-MS showed that the raw materials disappeared and detected the MS value of the boric acid corresponding to 13J. The product was judged to be borate according to TLC experience. The reaction mixture was filtered and concentrated to give the crude product of compound 13J, which was directly used in the next step without further purification.

Relevant characterization data: LCMS m/z: 175.1 [M+H]

Synthesis of Intermediate 14K:

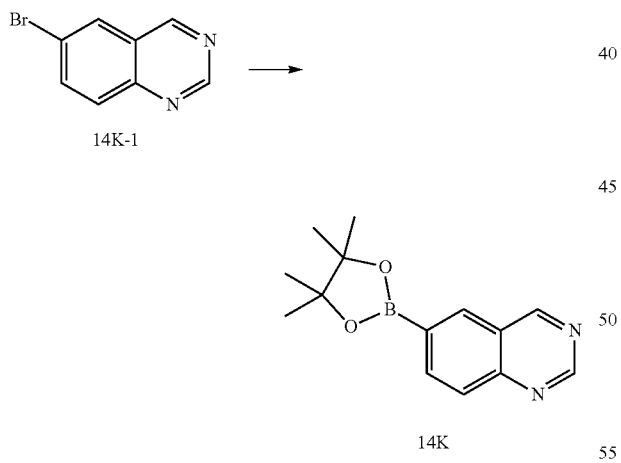

Raw materials 14K-1 (200 mg, 956.74 μmol, 1 eq), bis(pinacolato)diboron (267.25 mg, 1.05 mmol, 1.1 eq), potassium acetate (187.79 mg, 1.91 mmol, 2 eq), Pd(dppf)$_2$Cl$_2$ (62.36 mg, 95.67 μmol, 0.1 eq) were added into 1,4-dioxane, the mixture was heated to 80° C. under nitrogen protection and stirred at 80° C. for 4 hours. LCMS showed that the raw materials disappeared and detected the MS value of the boric acid corresponding to 14K. The reaction mixture was filtered, concentrated and purified by silica gel preparative plate (SiO$_2$, EA/PE=3/1) to give 14K.

Relevant characterization data: LCMS m/z: 175.2 [M+H].

Synthesis of Intermediate 17M:

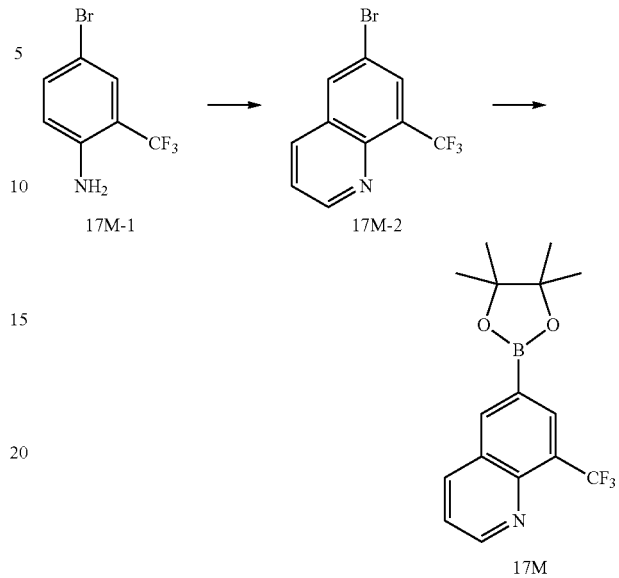

Step 1 (Synthesis of Compound 17M-2)

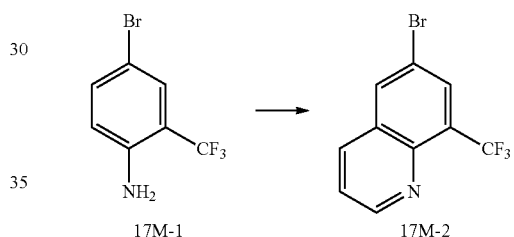

Glycerol (2.88 g, 31.25 mmol, 2.34 mL, 1.5 eq) was added to a solution of compound 17M-1 (5 g, 20.83 mmol, 2.92 mL, 1 eq) and sodium iodide (62.45 mg, 416.63 μmol, 0.02 eq) in concentrated sulfuric acid (20 mL), and the reaction was stirred at 110° C. for 5 hours, then heated to 120° C. and stirred for 12 hours. The reaction mixture was slowly poured into ice water (30 mL), extracted with ethyl acetate (25 mL*3). The organic phases were combined and washed with saturated brine (25 mL*2), dried over anhydrous sodium sulfate, filtered, and evaporated to dryness to give the crude product of compound 17M-2.

Relevant characterization data: LCMS m/z: 275.9 [M+H].

Step 2 (Synthesis of Compound 17M)

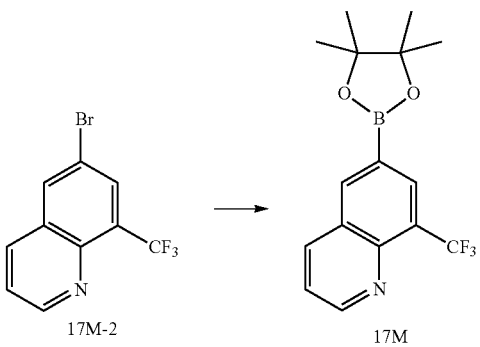 [SMILES: FC(F)(F)c1cc(Br)cc2cccnc12 ; CC1(C)OB(c2cc(C(F)(F)F)c3ncccc3c2)OC1(C)C]

Under nitrogen protection, a solution of compound 17M-2 (1 g, 3.62 mmol, 1 eq), pinacol borate (4.60 g, 18.11 mmol, 5 eq), potassium acetate (1.07 g, 10.87 mmol, 3 eq) and Pd(dbcp)$_2$Cl$_2$ (118.05 mg, 181.13 μmol, 0.05 eq) in dioxane (50 mL) was stirred at 90° C. for 30 minutes. The reaction mixture was cooled to room temperature and filtered. The filtrate was evaporated to dryness. The residue was separated and purified by column chromatography (PE/ethyl acetate=40/1, 100-200 mesh silica gel) to give the crude product of compound 17M.

Relevant characterization data: LCMS m/z: 324.1 [M+H].

Synthesis of Intermediate 18N:

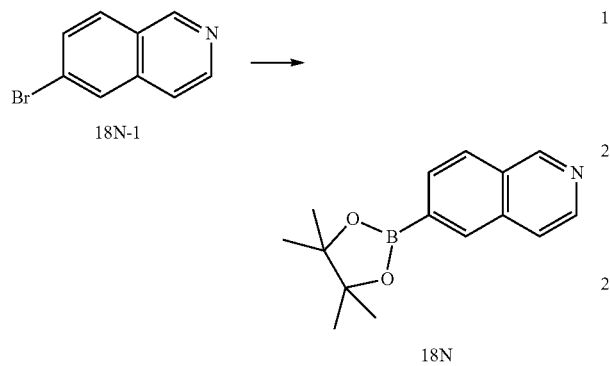

Raw materials 18N-1 (500 mg, 2.40 mmol, 1 eq), bis (pinacolato)diboron (610.27 mg, 2.40 mmol, 1 eq), Pd(dppf)$_2$Cl$_2$ (175.85 mg, 240.32 μmol, 0.1 eq), potassium acetate (471.70 mg, 4.81 mmol, 2 eq) were dissolved in 1,4-dioxane (22 mL), the mixture was heated to 90° C. under nitrogen protection and stirred at 90° C. for 10 hours. LCMS showed that the raw materials disappeared and detected the MS value of the boric acid corresponding to 18N. The product was judged to be borate according to TLC experience. The reaction was filtered and concentrated to give a crude product of compound 18N.

Relevant characterization data: LCMS m/z: 174.2 [M+H].

Synthesis of Intermediate 19O:

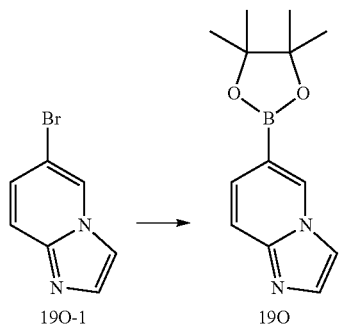 [SMILES: Brc1ccc2nccn2c1 ; CC1(C)OB(c2ccc3nccn3c2)OC1(C)C]

Pinacol borate (3.09 g, 12.18 mmol, 1.2 eq) and potassium acetate (2.99 g, 30.45 mmol, 3 eq) were added to a solution of compound 19O-1 (2.0 g, 10.15 mmol, 1 eq) in 1,4-dioxane (30 mL), and the mixture was purged three times with nitrogen, then Pd(pph$_3$)$_2$Cl$_2$ (712.47 mg, 1.02 mmol, 0.1 eq) was added. The system was purged with nitrogen several times, then heated to 90° C. and stirred for 1.5 hours. LCMS showed that the raw materials disappeared and detected the MS value of the boric acid corresponding to 19O. The product was judged to be borate according to TLC experience. The reaction mixture was cooled and filtered, and the filtrate was concentrated to give a crude product of compound 19O crude product, which was directly used in the next step without further purification.

Relevant characterization data: LCMS m/z: 163.3 [M+H].

Synthesis of Intermediate 21Q:

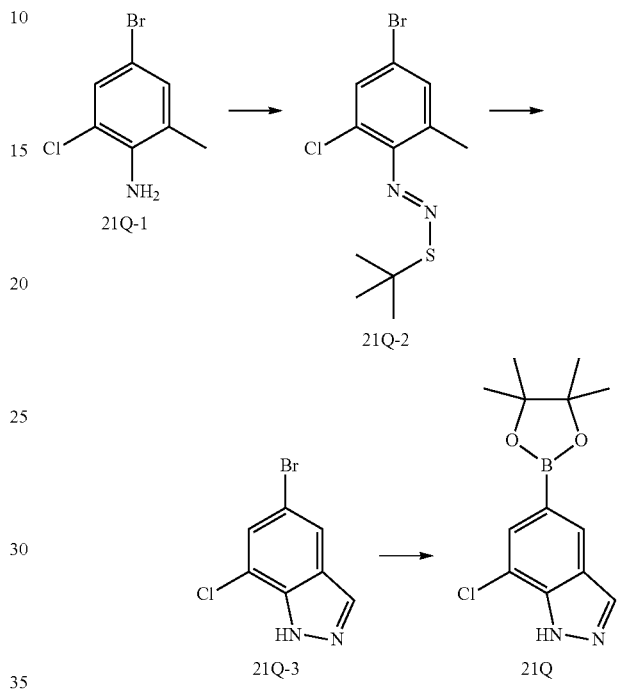

Step 1 (Synthesis of Compound 21Q-2)

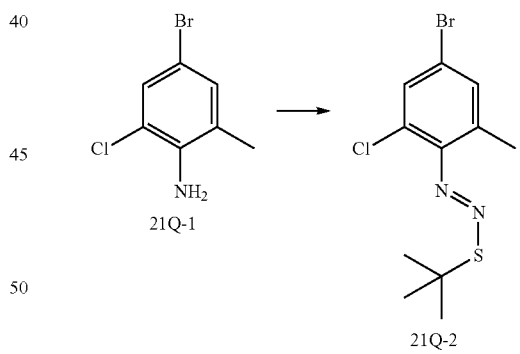

An aqueous solution (2 mL) of sodium nitrite (1.31 g, 19.05 mmol, 1.05 eq) was slowly added dropwise to a hydrochloric acid aqueous solution of compound 21Q-1 (4 g, 18.14 mmol, 1 eq) (5 mL, weight content 24%) at −5° C. The mixture was stirred for 30 minutes and adjusted to pH 5 by addition of solid sodium acetate. Then an ethanol solution (20 mL) of tert-butyl mercaptan (1.64 g, 18.14 mmol, 2.04 mL, 1 eq) was added into the reaction mixture at 0° C. The reaction mixture was stirred for 1 hour. LCMS showed that the raw materials disappeared and the product formed. The reaction mixture was quenched by adding ice water and precipitation formed. The mixture was filtered and the filter cake was washed with water and dried to give a crude product of compound 21Q-2 which was directly used in the next step without further purification.

Relevant characterization data: LCMS m/z: 322.9 [M+H].

Step 2 (Synthesis of Compound 21Q-3)

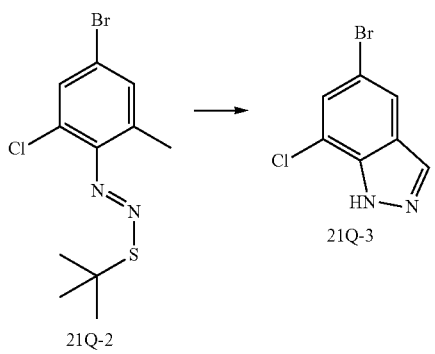 [SMILES: Cc1cc(Br)cc(Cl)c1/N=N/SC(C)(C)C ; Clc1cc(Br)cc2cn[nH]c12]

Potassium tert-butoxide (10.26 g, 91.40 mmol, 10 eq) was added to a solution of compound 21Q-2 (3 g, 9.14 mmol, 1 eq) in dimethyl sulfoxide (35 mL) and the mixture was stirred at 25° C. for 30 minutes. TLC showed that the raw materials disappeared and LCMS detected the formation of the product. The reaction mixture was diluted with water (50 mL), and extracted with ethyl acetate (35 mL*3). The organic phases were combined and washed with saturated brine (35 mL*2), dried over anhydrous sodium sulfate, filtered, and evaporated to dryness to give a crude product of compound 21Q-3, which was directly used in the next step without further purification.

Relevant characterization data: LCMS m/z: 232.9 [M+H].

Step 3 (Synthesis of Compound 21Q)

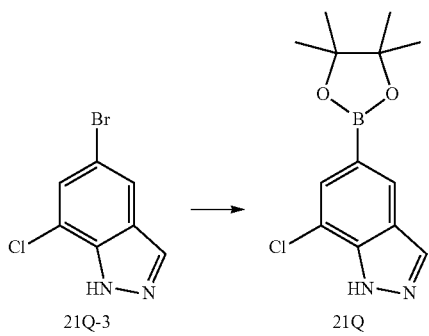 [SMILES: Clc1cc(Br)cc2cn[nH]c12 ; CC1(C)OB(c2cc(Cl)c3[nH]ncc3c2)OC1(C)C]

A solution of compound 21Q-3 (0.5 g, 2.16 mmol, 1 eq), pinacol borate (877.63 mg, 3.46 mmol, 1.6 eq), potassium acetate (635.97 mg, 6.48 mmol, 3 eq) and Pd(dppf)$_2$Cl$_2$ (79.03 mg, 108.00 μmol, 0.05 eq) in dimethylsulfoxide (2 mL) were stirred under microwave at 120° C. for 1 hour. LCMS detected the formation of product. The reaction mixture was cooled to room temperature, filtered, and the filtrate was evaporated to dryness. The crude product was separated and purified by column chromatography (PE/ethyl acetate=10/1 to 5/1) to give a crude product of compound 21Q, which was directly used in the next step.

Relevant characterization data: LCMS m/z: 279.1 [M+H].

Synthesis of Intermediate 22R:

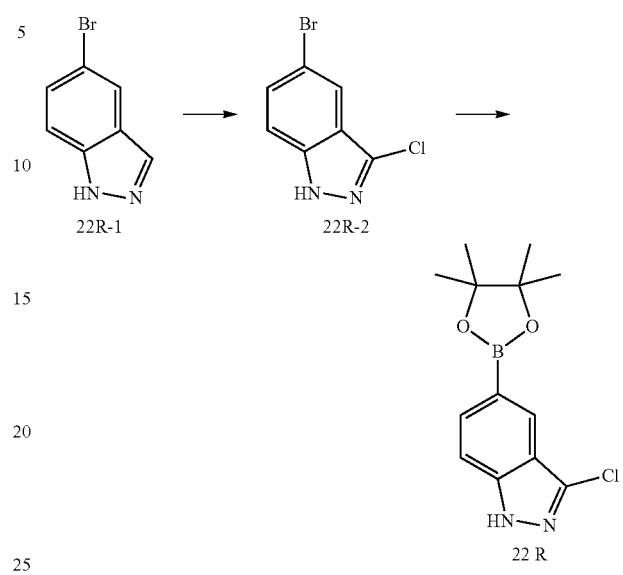

Step 1 (Synthesis of Compound 22R-2)

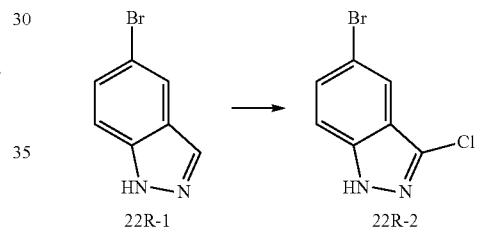

NCS (745.49 mg, 5.58 mmol, 1.1 eq) was added to an acetonitrile solution (10 mL) of compound 22R-1 (1 g, 5.08 mmol, 1 eq), and the reaction mixture was stirred at 60° C. for 5 hours. LC-MS showed that the raw materials disappeared and the product formed. The reaction mixture was cooled to room temperature, diluted with water (20 mL), extracted with ethyl acetate (20 mL*3). The organic phases were combined and washed with saturated brine (20 mL*2), dried over anhydrous sodium sulfate, filtered, and evaporated to dryness to give a crude product of compound 22R-2.

Relevant characterization data: LCMS m/z: 232.9 [M+H].

Step 2 (Synthesis of Compound 22R)

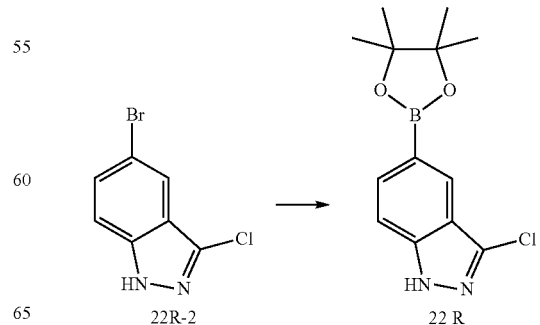

Under nitrogen protection, a dioxane solution (10 mL) of compound 22R-2 (0.2 g, 864.02 μmol, 1 eq), pinacol borate (438.81 mg, 1.73 mmol, 2 eq), potassium acetate (169.59 mg, 1.73 mmol, 2 eq) and Pd(dppf)$_2$Cl$_2$ (56.31 mg, 86.40 μmol, 0.1 eq) was stirred at 90° C. for 12 hours. The reaction mixture was cooled to room temperature, filtered, and the filtrate was evaporated to dryness. The residue was separated and purified by column chromatography (PE/ethyl acetate=10:1 to 5:1) to give a crude product of compound 22R.

Relevant characterization data: LCMS m/z: 279.1 [M+H].

Synthesis of Intermediate 23S:

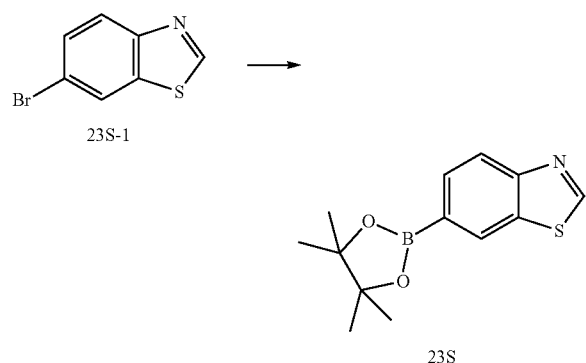

Raw materials 23S-1 (500 mg, 2.34 mmol, 1 eq), bis(pinacolato)diboron (652.39 mg, 2.57 mmol, 1.1 eq), Pd(dppf)$_2$Cl$_2$ (170.89 mg, 233.56 μmol, 0.1 eq), potassium acetate (458.43 mg, 4.67 mmol, 2 eq) were dissolved in 1,4-dioxane (22 mL), the mixture was heated to 80° C. under nitrogen protection and stirred at 80° C. for 10 hours. LC-MS showed that the raw materials disappeared and the product formed. The mixture was filtered and concentrated to give a crude product of 23S, which was directly used in the next step without further purification.

Relevant characterization data: LCMS m/z: 262.0 [M+H].

Synthesis of Intermediate 34-3

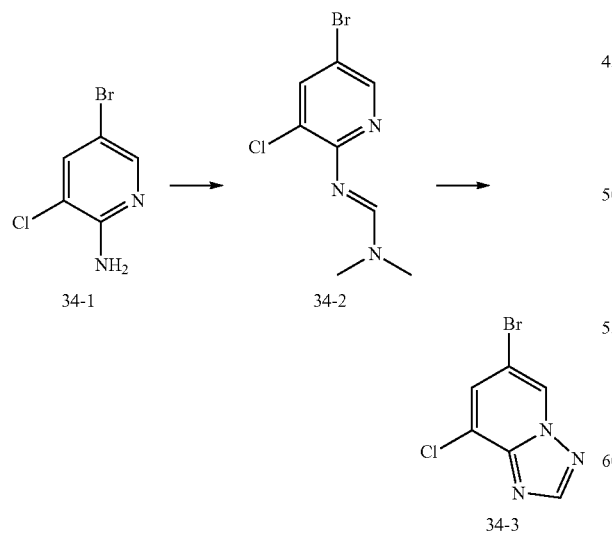

Step 1 (Synthesis of Compound 34-2)

Compound 34-1 (2.0 g, 9.64 mmol, 1 eq) and DMF-DMA (1.72 g, 14.46 mmol, 1.5 eq) were dissolved in methanol (50 mL), and the reaction mixture was heated to 70° C. and stirred for 6.5 hours. LCMS showed that the raw materials disappeared and the product formed. The reaction mixture was cooled and evaporated under reduced pressure to remove methanol to give compound 34-2. The crude product was directly used in the next step without further purification.

Relevant characterization data: LCMS m/z: 264.0 [M+H].

Step 2 (Synthesis of Compound 34-3)

Compound 34-2 (2.49 g, 9.48 mmol, 1 eq) was dissolved in methanol (40 mL) and cooled to 0° C., then pyridine (1.50 g, 18.97 mmol, 1.53 mL, 2 eq) and hydroxylamine sulfonic acid (1.39 g, 12.33 mmol, 1.3 eq) were added under nitrogen protection. The mixture was slowly raised to 25° C. and stirred for 4 hours, then heated to 70° C. and stirred for 1 hour. LCMS showed that the raw materials disappeared and the product formed. The reaction mixture was concentrated and diluted with ethyl acetate (20 mL), and saturated sodium bicarbonate solution (15 mL) was added. The mixed solution was extracted with ethyl acetate (20 mL*3). The organic phases were combined, dried over sodium sulfate, filtered, concentrated, and purified by silica gel column (PE: EA=8/1 to 6/1) to give compound 34-3.

Relevant characterization data: LCMS m/z: 234.1 [M+H].

Embodiment 1

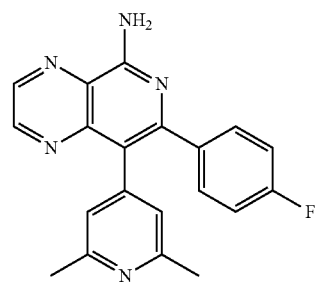 [SMILES: Cc1cc(-c2c(-c3ccc(F)cc3)nc(N)c3nccnc23)cc(Cl)n1]

Embodiment 1

Synthesis Embodiment 1 used (1-1) as the initial raw material, the detailed synthesis route 1 is as follows:

Route 1

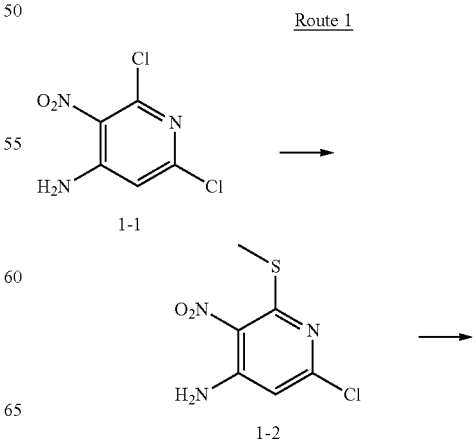

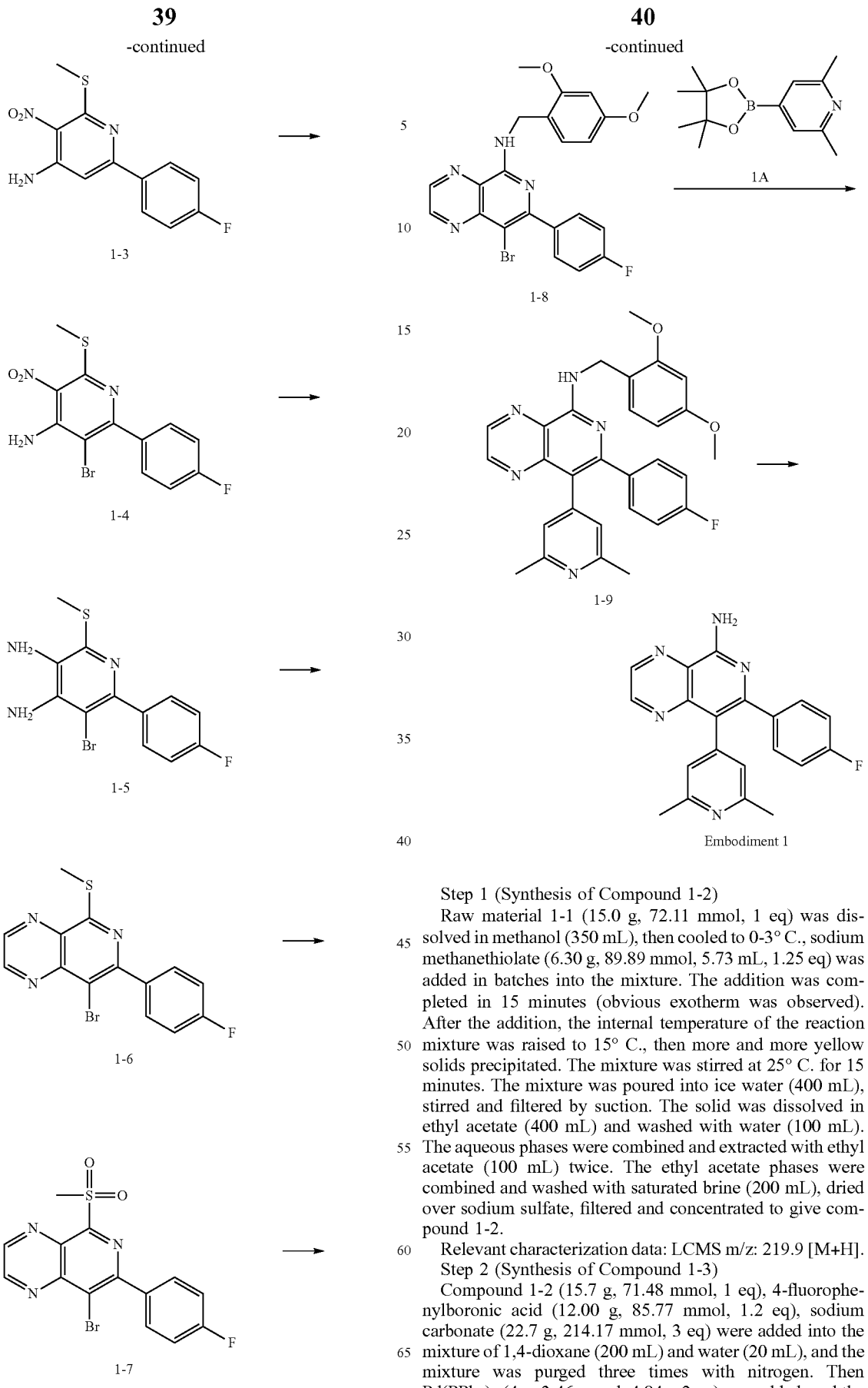

Step 1 (Synthesis of Compound 1-2)

Raw material 1-1 (15.0 g, 72.11 mmol, 1 eq) was dissolved in methanol (350 mL), then cooled to 0-3° C., sodium methanethiolate (6.30 g, 89.89 mmol, 5.73 mL, 1.25 eq) was added in batches into the mixture. The addition was completed in 15 minutes (obvious exotherm was observed). After the addition, the internal temperature of the reaction mixture was raised to 15° C., then more and more yellow solids precipitated. The mixture was stirred at 25° C. for 15 minutes. The mixture was poured into ice water (400 mL), stirred and filtered by suction. The solid was dissolved in ethyl acetate (400 mL) and washed with water (100 mL). The aqueous phases were combined and extracted with ethyl acetate (100 mL) twice. The ethyl acetate phases were combined and washed with saturated brine (200 mL), dried over sodium sulfate, filtered and concentrated to give compound 1-2.

Relevant characterization data: LCMS m/z: 219.9 [M+H].

Step 2 (Synthesis of Compound 1-3)

Compound 1-2 (15.7 g, 71.48 mmol, 1 eq), 4-fluorophenylboronic acid (12.00 g, 85.77 mmol, 1.2 eq), sodium carbonate (22.7 g, 214.17 mmol, 3 eq) were added into the mixture of 1,4-dioxane (200 mL) and water (20 mL), and the mixture was purged three times with nitrogen. Then Pd(PPh$_3$)$_4$ (4 g, 3.46 mmol, 4.84 e-2 eq) was added, and the system was purged with nitrogen several times and then heated to 90-100° C. and stirred for 12 hours. The reaction mixture was cooled and evaporated under reduced pressure to remove 1,4-dioxane, the residue was diluted with water (200 mL) and ethyl acetate (300 mL). The aqueous phase was separated and extracted with ethyl acetate (200 mL) twice. The ethyl acetate phases were combined and washed with brine (200 mL), dried over sodium sulfate, filtered, then combined with the previous batch, concentrated, triturated with PE/ethyl acetate (10:1, 400 mL) then filtered and dried to give compound 1-3, which was directly used in the next step.

Relevant characterization data: LCMS m/z: 280.2 [M+H].

Step 3 (Synthesis of Compounds 1-4)

Compound 1-3 (17.4 g, 50.04 mmol, 1 eq) was added to acetonitrile (350 mL), then cooled to 0° C. NBS (11.5 g, 64.61 mmol, 1.29 eq) was added in batches under nitrogen protection, and the mixture immediately turned dark brown. The mixture was slowly raised to 25° C. and reacted for 15 hours. The reaction mixture was quenched with 10% sodium thiosulfate solution (200 mL), and the precipitated yellow solid was filtered and rinsed with water (30 mL) to give a partial product of compound 1-4. The filtrate was extracted once with ethyl acetate (100 mL). The organic phase was washed once with water (100 mL) and once with brine (100 mL), dried over sodium sulfate, filtered and concentrated to give a yellow solid, which was triturated with acetonitrile (200 mL), filtered and dried to give the product. The two parts of solid were combined and dried in vacuum to give compound 1-4

Relevant characterization data: LCMS m/z: 358.1 [M+H].

Step 4 (Synthesis of Compound 1-5)

Compound 1-4 (14.2 g, 39.64 mmol, 1 eq) was suspended in methanol (150 mL), iron powder (11.0 g, 196.97 mmol, 4.97 eq) was added. Then concentrated hydrochloric acid (60 mL, 15.24 eq) was added dropwise at 0-15° C., and the addition was completed in 15 minutes. After the addition, the reaction mixture was raised to 25-30° C. and stirred for 14 hours, then iron powder (2.2 g, 39.39 mmol) and concentrated hydrochloric acid (10 mL, 2.54 eq) were additionally added, and the reaction mixture was continuously stirred at 25-30° C. for 2 hours. The mixture was filtered through diatomite, then rinsed with methanol (20 mL). The filtrate was adjusted to pH 8 with 20% sodium hydroxide solution (300 mL) (blue solid precipitated at this time, and the solid was obtained by filtration), then ethyl acetate (500 mL) was added to the filtrate and the mixture was stirred for 30 minutes. The mixture was filtered through diatomite. The organic phase was separated and washed with brine (200 mL), dried over sodium sulfate, then filtered and concentrated to give a solid. The two parts of solid were combined and dried in vacuum to give compound 1-5.

Relevant characterization data: LCMS m/z: 328.0 [M+H].

Step 5 (Synthesis of Compounds 1-6)

Compound 1-5 (21.0 g, 63.98 mmol, 1 eq) was suspended in ethanol (250 mL), 40% acetaldehyde solution (13.88 g, 95.63 mmol, 12.5 mL, 1.49 eq) was added to the suspension under nitrogen protection. The reaction mixture was stirred at 90-100° C. for 2 hours, then cooled to 25° C., and a solid precipitated. The mixture was filtered, and the filter cake was washed with cold ethanol (20 mL) and dried in vacuum to give compound 1-6.

Relevant characterization data: LCMS m/z: 351.0 [M+H].

$^1$H NMR (DMSO-d$_6$, 400 MHz) δ 9.33 (s, 1H), 9.07 (d, J=1.6 Hz, 1H), 7.95-7.92 (m, 2H), 7.42-7.37 (m, 2H), 2.61 (s, 3H).

Step 6 (Synthesis of Compound 1-7)

At room temperature, m-chloroperoxybenzoic acid (17.39 g, 85.66 mmol, purity 85%, 3.0 eq) was added to a mixture of dichloromethane (200 mL) and compound 1-6 (10 g, 28.55 mmol, 1 eq). The mixture was stirred at room temperature for 10 minutes, then dichloromethane (150 mL) was added. The mixture was filtered and the filtrate was washed with water (100 mL*3), saturated sodium sulfite solution (50 mL*3) and brine (50 mL), dried over sodium sulfate solid, then filtered and concentrated to give compound 1-7.

Relevant characterization data: LCMS m/z: 383.9 [M+1].

Step 7 (Synthesis of Compound 1-8)

N,N-Diisopropylethylamine (6.59 g, 51.02 mmol, 8.89 mL, 2.5 eq) and 2,4-dimethoxybenzylamine (4.09 g, 24.49 mmol, 3.69 mL, 1.2 eq) were added to a mixture of isopropanol (300 mL) and compound 1-7 (7.8 g, 20.41 mmol, 1 eq), the mixture was heated to 80° C. and stirred at 80° C. for 8 hours. TLC (SiO$_2$, PE/ethyl acetate=3/1) showed that the raw materials completely disappeared, and detected the formation of a new point, indicating the reaction was completed. The mixture was concentrated, then ethanol (20 mL) was added, and a large amount of yellow solid was present. The mixture was filtered, and the filter cake was washed with ethanol (10 mL*3) to give a solid. The filtrate was concentrated to give a yellow solid, which was also washed with ethanol (10 mL*3). The two parts of solid were combined and dried in vacuum to give compound 1-8, which was directly used in the next step.

Step 8 (Synthesis of Compound 1-9)

1,4-Dioxane (10 mL) and water (2 mL) were added into compound 1-8 (1.0 g, 2.13 mmol, 1.0 eq), followed by addition of 2,6-dimethyl-4-pyridineboronic acid (386.03 μmg, 2.56 μmmol, 1.2 eq, compound 1A), [1,1-bis (diphenylphosphino)ferrocene]palladium dichloride (II) dichloromethane complex (348.02 mg, 426.16 μmol, 0.2 eq) and potassium carbonate (883.50 mg, 6.39 mmol, 3.0 eq). The mixture was heated to 90° C. under nitrogen protection and stirred at 90° C. for 30 minutes. The mixture was concentrated and purified by column (SiO$_2$, PE/ethyl acetate volume ratio 1/1) to give compound 1-9 as a brown oil.

Relevant characterization data: LCMS m/z: 496.1 [M+H].

Step 9 (Synthesis of Embodiment 1)

Compound 1-9 (200 mg, 403.59 μmol, 1 eq) was added to trifluoroacetic acid (3 mL), the mixture was heated to 70° C. and stirred at 70° C. for 2 hours. The mixture was concentrated, and purified by reverse phase column (column: Phenomenex Luna Phenyl-Hexyl 150*30 mm 5 um; Mobile phase: [Water (10 mM ammonium bicarbonate)-acetonitrile]; B %: 35%-65%, 3 min)) to give Embodiment 1.

Relevant characterization data: LCMS m/z: 346.0 [M+H].

$^1$H NMR (400 MHz, CD$_3$OD) δ 8.87 (d, J=2.0 Hz, 1H), 8.77 (d, J=2.0 Hz, 1H), 7.45-7.30 (m, 2H), 6.98 (m, 2H), 6.92 (s, 2H), 2.38 (s, 6H).

The embodiment compounds listed in table 1 were prepared by the steps similar to route 1 of preparation embodiment 1, except that the boric acid derivative in the following table was used as the raw material in step 8 instead of the raw material 1A to give the corresponding compound.

TABLE 1

| Product identifier | Product structure | Chemical structure and identifier of raw material | Product LCMS m/z: [M + H] | ¹H NMR of product |
|---|---|---|---|---|
| Embodiment 2 | (pyrido-pyrazine amine with 4-fluorophenyl and 2-chloro-6-methylpyridinyl substituents) | 2B (2-chloro-6-methyl-4-pyridinyl pinacol boronate) | 366.0 | ¹H NMR (400 MHz, METHANOL-d₄) δ = 8.90 (d, J = 2.0 Hz, 1H), 8.78 (d, J = 2.0 Hz, 1H), 7.45-7.29 (m, 2H), 7.15-6.97 (m, 4H), 2.51-2.24 (s, 3H). |
| Embodiment 3 | (pyrido-pyrazine amine with 4-fluorophenyl and 2-chloro-6-trifluoromethylpyridinyl substituents) | 3C (2-chloro-6-trifluoromethyl-4-pyridinyl pinacol boronate) | 420.0 | ¹H NMR (400 MHz, METHANOL-d₄) δ = 8.90 (d, J = 2.0 Hz, 1H), 8.78 (d, J = 2.0 Hz, 1H), 7.45-7.29 (m, 2H), 7.15-6.97 (m, 4H), 2.51-2.24 (s, 3H) |
| Embodiment 4 | (pyrido-pyrazine amine with 4-fluorophenyl and quinolin-6-yl substituents) | 4D (quinolin-6-yl boronic acid) | 368.1 | ¹H NMR (400 MHz, DMSO-d₆) δ = 4.47 (s, 1H), 4.37 (br d, J = 15.4 Hz, 2H), 3.73 (d, J = 8.2 Hz, 1H), 3.43 (d, J = 8.0 Hz, 1H), 3.27 (s, 1H), 3.09 (d, J = 8.5 Hz, 1H), 3.01 (s, 2H), 2.98 (s, 1H), 2.87 (br d, J = 5.1 Hz, 2H), 2.51 (t, J = 8.9 Hz, 2H) |
| Embodiment 5 | (pyrido-pyrazine amine with 4-fluorophenyl and quinoxalin-6-yl substituents) | 5E (quinoxalin-6-yl pinacol boronate) | 369.1 | ¹H NMR (400 MHz, DMSO-d₆) δ = 8.99 (s, 1H), 8.96-8.84 (m, 3H), 8.01 (d, J = 8.8 Hz, 1H), 7.90 (s, 1H), 7.70 (d, J = 8.5 Hz, 1H), 7.58 (s, 2H), 7.39 (dd, J = 6.0, 8.2 Hz, 2H), 7.03 (t, J = 8.7 Hz, 2H) |

TABLE 1-continued

| Product identifier | Product structure | Chemical structure and identifier of raw material | Product LCMS m/z: [M + H] | ¹H NMR of product |
|---|---|---|---|---|
| Embodiment 6 | | 6F | 358.1 | ¹H NMR (400 MHz, DMSO-$d_6$) δ = 9.01 (d, J = 1.9 Hz, 1H), 8.87 (d, J = 1.8 Hz, 1H), 8.79 (s, 1H), 8.48 (s, 1H), 7.76 (d, J = 9.2 Hz, 1H), 7.64 (s, 2H), 7.50-7.39 (m, 3H), 7.10 (t, J = 8.8 Hz, 2H) |
| Embodiment 7 | | 7G | 358.2 | ¹H NMR (400 MHz, DMSO-$d_6$) δ = 9.00 (d, J = 1.9 Hz, 1H), 8.89-8.83 (m, 2H), 8.46 (s, 1H), 7.64 (br d, J = 5.1 Hz, 3H), 7.47-7.41 (m, 2H), 7.10 (t, J = 8.9 Hz, 2H), 7.01 (dd, J = 1.7, 7.0 Hz, 1H) |
| Embodiment 8 | | 8H | 372.1 | ¹H NMR (400 MHz, CHLOROFORM-d) δ = 8.96 (d, J = 1.8 Hz, 1H), 8.65 (d, J = 1.8 Hz, 1H), 7.45-7.36 (m, 2H), 6.99-6.87 (m, 2H), 6.82-6.73 (m, 2H), 6.42 (d, J = 8.0 Hz, 1H), 6.02 (br s, 2H), 3.37-3.26 (m, 2H), 2.67 (m, 2H), 1.97-1.90 (m, 2H) |
| Embodiment 9 | | 9I | 358.0 | ¹H NMR (400 MHz, DMSO-$d_6$) δ = 9.19 (s, 1H), 9.00 (d, J = 1.6 Hz, 1H), 8.86 (s, 1H), 8.36 (s, 1H), 7.73-7.65 (m, 1H), 7.61 (s, 2H), 7.50-7.42 (m, 2H), 7.23-7.15 (m, 1H), 7.13-7.08 (m, 2H). |

The Preparation of Hydrochloride of the Compound was Exemplified by Embodiment 6:

200 mL of acetonitrile and 200 mL of water were added to a reaction flask at 25° C., then the free base of Embodiment 6 (6 g) was added, followed by addition of 1M dilute hydrochloric acid to adjust the pH value to 3-5. The reaction mixture was stirred at 25° C. for 0.5 hour. The Embodiment 6 hydrochloride was obtained.

Product LCMS m/z: [M+H] 358.2

¹H NMR (400 MHz, DMSO-$d_6$) δ=9.24 (t, J=3.6 Hz, 1H), 9.12 (d, J=2.0 Hz, 1H), 8.87 (s, 1H), 8.59 (t, J=5.2 Hz, 1H), 7.84 (t, J=8.4 Hz, 1H), 7.58-7.55 (m, 2H), 7.50 (d, J=15.6 Hz, 1H), 7.27 (t, J=9.2 Hz, 2H).

Embodiment 10

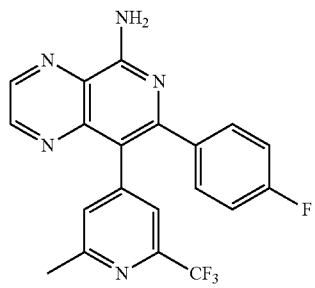

Synthesis Embodiment 2 used (1-6) as the initial raw material, the detailed synthesis route was as follows:

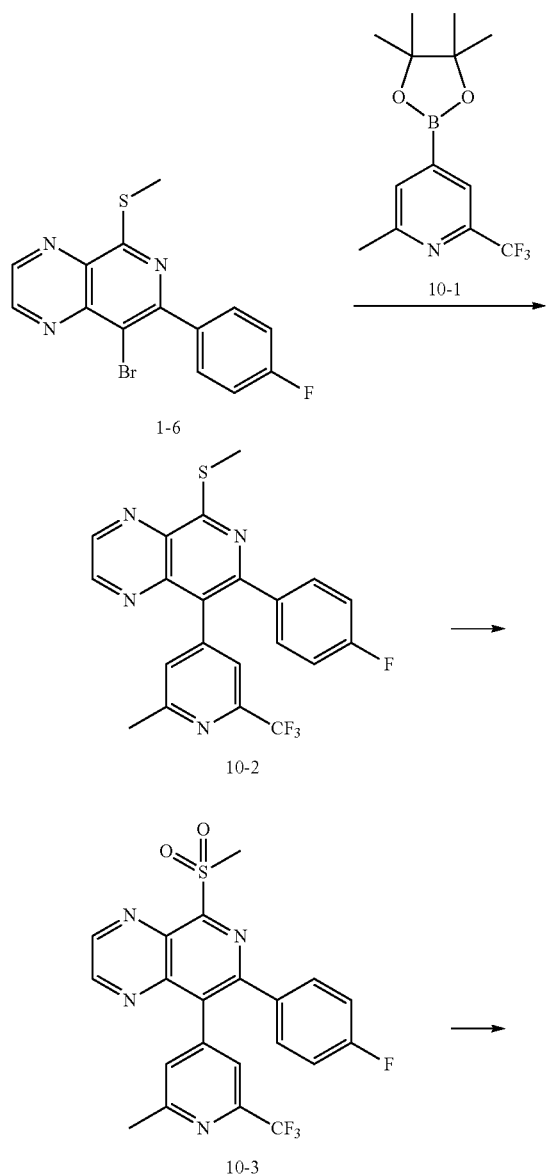

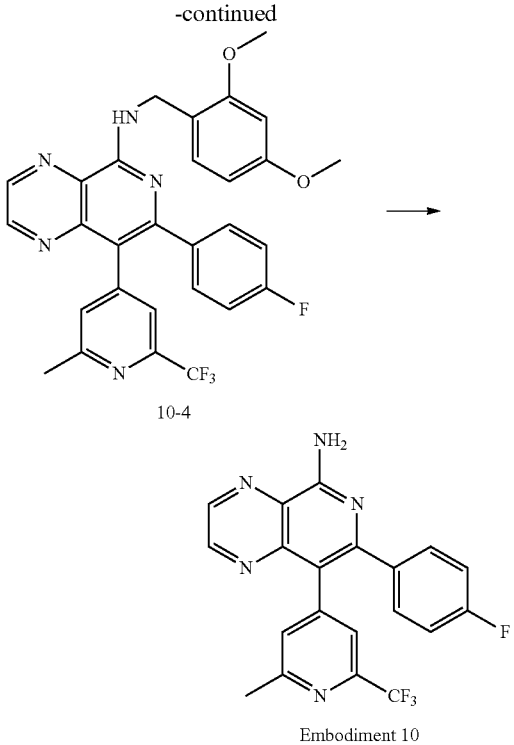

Step 1 (Synthesis of Compound 10-2)

Ferrocene palladium dichloride (208.94 mg, 285.54 μmol, 0.1 eq), potassium carbonate (789.30 mg, 5.71 mmol, 2 eq), 2-methyl-6-trifluoromethyl-4-pinacol borate (983.71 mg, 3.43 mmol, 1.2 eq) were added to a solution of compound 1-6 (1.0 g, 2.86 mmol, 1 eq) in 1,4-dioxane (20 mL) and water (4 mL), the mixture was purged with nitrogen three times and stirred at 90° C. for 2 hours. When LCMS showed that the reaction was completed, the reaction mixture was concentrated to give a crude product, which was purified by a silica gel column (100-200 mesh silica gel, gradient elution with PE/ethyl acetate volume ratio of 10/1 to 5/1) to give compound 10-2.

Relevant characterization data: LCMS m/z: 431.0 [M+H].

Step 2 (Synthesis of Compound 10-3)

m-Chloroperoxybenzoic acid (1.71 g, 8.42 mmol, purity 85%, 2.5 eq) was added into a solution of compound 10-2 (1.45 g, 3.37 mmol, 1 eq) in dichloromethane (2 mL) at 10° C., and the reaction mixture was stirred at 25° C. for 20 minutes. After LCMS showed that the reaction was complete, saturated sodium bicarbonate (20 mL) and saturated sodium sulfite (20 mL) were added to the reaction mixture and the resulting mixture was extracted with dichloromethane (30 mL*2). The organic phase was washed with saturated brine, dried over anhydrous sodium sulfate, and concentrated under reduced pressure to give compound 10-3.

Relevant characterization data: LCMS m/z: 463.0 [M+H].

Step 3 (Synthesis of Compound 10-4)

Diisopropylethylamine (877.61 mg, 6.79 mmol, 1.18 ml, 2 eq) and 2,4-dimethoxybenzylamine (851.54 mg, 5.09 mmol, 767.15 μL, 1.5 eq) were added to a solution of compound 10-3 (1.57 g, 3.40 mmol, 1 eq) in isopropanol (20 mL), and the reaction mixture was stirred at 85° C. for 17 hours. After LCMS showed that the reaction was complete, the reaction mixture was concentrated to dryness, then water (50 mL) was added. The mixture was extracted with ethyl acetate (50 mL*2). The combined organic phase was washed with saturated brine, dried over anhydrous sodium sulfate, filtered and concentrated to give a crude product of compound 10-4 (2.4 g).

Relevant characterization data: LCMS m/z: 550.0 [M+H].

Step 4 (Synthesis of Embodiment 10)

A solution of compound 10-4 (2.4 g, 4.37 mmol, 1 eq) in trifluoroacetic acid (20 mL) was stirred at 90° C. for 2 hours. The mixture was concentrated under reduced pressure to dryness, then adjusted to pH 8 with saturated potassium carbonate solution, extracted with ethyl acetate (30 mL*2). The organic phase was washed with saturated brine, dried over anhydrous sodium sulfate, filtered, concentrated, and purified by preparative chromatography column to give Embodiment 10.

Relevant characterization data: LCMS m/z: 400.0 [M+H].

$^1$H NMR (DMSO-d$_6$) δ 9.10 (d, J=1.6 Hz, 1H), 9.01 (d, J=1.6 Hz, 1H), 7.69 (s, 2H), 7.42 (s, 2H), 7.36-7.34 (m, 2H), 7.14-7.09 (m, 2H), 2.48 (s, 3H);

Embodiment 11

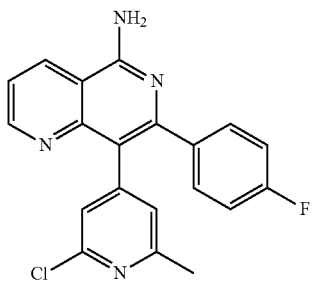

Embodiment 11

Synthesis Embodiment 11 used (11-1) as the initial raw material, the detailed synthesis route was as follows:

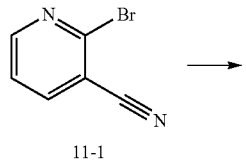

11-1

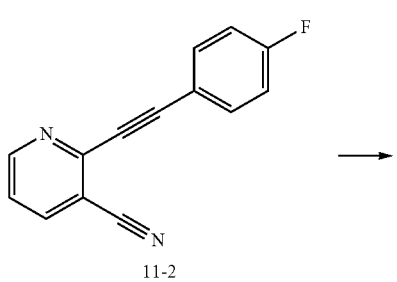

11-2

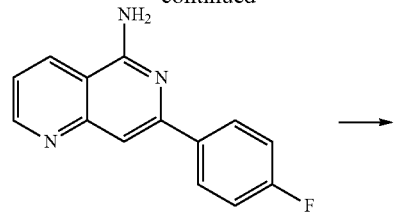

11-3

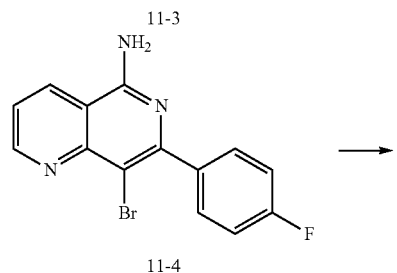

11-4

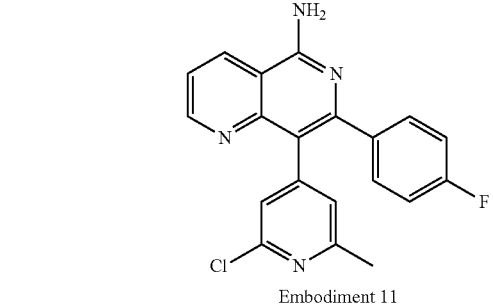

Embodiment 11

Step 1 (Synthesis of Compound 11-2)

A solution of Compound 11-1 (0.4 μg, 2.19 μmmol, 1 eq), 4-fluorophenylacetylene (525.11 mg, 4.37 mmol, 500.11 μL, 2 eq), Pd(PPh$_3$)$_2$Cl$_2$ (306.83 mg, 437.15 μmol, 0.2 eq), cuprous iodide (83.25 mg, 437.15 μmol, 0.2 eq) and triethylamine (884.70 mg, 8.74 mmol, 1.22 mL, 4 eq) in N,N-dimethylformamide (10 mL) was purged three times with nitrogen in vacuum, and then stirred at 25° C. for 1.5 hours under nitrogen atmosphere. After LC-MS showed that the reaction was complete, 20 mL of water and 30 mL of ethyl acetate were added to the reaction mixture, and the mixture was partitioned. The organic phase was dried over anhydrous sodium sulfate, filtered, concentrated, and the residue was purified by silica gel column (mobile phase: PE/ethyl acetate volume ratio 9/1 to 6/1) to give compound 11-2.

Relevant characterization data: LCMS m/z: 223.0 [M+H].

$^1$H NMR (DMSO-d$_6$) δ 8.8 (d, J=4.8 Hz, 1H), 8.0 (d, J=7.6 Hz, 1H), 7.7 (dd, J=5.6, 8 Hz, 2H), 7.4 (dd, J=4.8, 7.6 Hz, 1H), 7.1 (t, J=8.4 Hz, 2H);

Step 2 (Synthesis of Compound 11-3)

Potassium carbonate (355.75 mg, 2.57 mmol, 1.3 eq) was added to a solution of compound 11-2 (0.44 g, 1.98 mmol, 1 eq) in N,N-dimethylformamide (10 mL) and aqueous ammonia (10 mL), and the resulting mixture was stirred at 80° C. for 16 hours. When LCMS showed that the reaction was complete, the reaction mixture was cooled to 25° C., then diluted with 30 mL of water and extracted with 40 mL of ethyl acetate. The organic phase was washed twice with 20 mL of water each time, then dried over anhydrous sodium sulfate, filtered, concentrated in vacuum to give the compound 12-3, compound 11-3 was directly used in the next step without further purification.

Relevant characterization data: LCMS m/z: 240.2 [M+H].

Step 3 (Synthesis of Compound 11-4)

At 0° C., N-bromosuccinimide (357.08 mg, 2.01 mmol, 1.2 eq) was added to a solution of compound 12-3 (0.4 g, 1.67 mmol, 1 eq) in acetonitrile (30 mL), and the resulting mixture was stirred at 25° C. for 2.5 hours. When LCMS showed that the reaction was complete, the reaction mixture was concentrated, and the residue obtained was triturated with mixed solution (20 mL, dichloromethane/PE=1/5) to give compound 11-4, which was directly used in the next step without further purification.

Relevant characterization data: LCMS m/z: 319.8 [M+H].

Step 4 (Synthesis of Embodiment 11)

After the mixed solution of compound 11-4 (0.05 g, 157.16 μmol, 1 eq) and 2-methyl-6-chloro-4-pyridineboronic acid (47.81 mg, 188.59 μmol, 1.2 eq) in dioxane (10 mL) and water (2 mL) was purged with nitrogen three times in vacuum, potassium phosphate (66.72 μmg, 314.32 μmol, 2 eq) and [1,1'-bis(di-tert-butylphosphino)ferrocene]palladium dichloride (20.49 mg, 31.43 μmol, 0.2 eq) were added, the resulting mixture was stirred at 90° C. for 2 hours under nitrogen protection.

After LCMS showed that the reaction was complete, the reaction mixture was concentrated in vacuum, the residue obtained was purified by silica gel column (PE/ethyl acetate=1/1), and then the residue was further purified by preparative column (Phenomenex Synergi C18 150*30 mm*4 μm; Mobile phase: [Water (0.05% hydrochloric acid)-acetonitrile]; B %: 20%-41%, 7 min) to give Embodiment 11.

Relevant characterization data: LCMS m/z: 364.9 [M+H].

$^1$H NMR (400 MHz, DMSO-$d_6$) δ=9.23 (dd, J=1.4, 8.4 Hz, 1H), 9.14 (d, J 4.8 Hz, 1H), 7.84 (dd, J=4.4, 8.4 Hz, 1H), 7.50-7.43 (m, 2H), 7.29 (t, J=8.8 Hz, 2H), 7.15 (s, 1H), 7.10 (s, 1H), 2.37 (s, 3H).

Embodiment 12

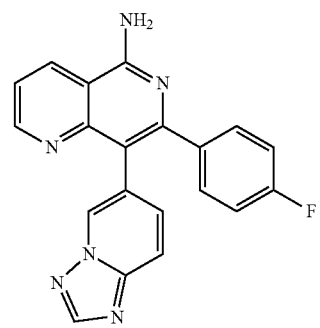

Embodiment 12

Embodiment 12 was prepared according to the steps similar to the route in the preparation Embodiment 11, except that raw material 6F was used in step 4 instead of raw material 2B (2-methyl-6-chloro-4-pyridineboronic acid) to give the corresponding Embodiment 12.

Relevant characterization data: LCMS m/z: 357.3 [M+H];

$^1$H NMR (400 MHz, DMSO-$d_6$) δ=8.90 (dd, J=1.6, 4.4 Hz, 1H), 8.77-8.68 (m, 2H), 8.45 (s, 1H), 7.74 (d, J=9.2 Hz, 1H), 7.56 (dd, J=4.4, 8.4 Hz, 1H), 7.50-7.37 (m, 5H), 7.14-7.02 (m, 2H).

The embodiment compounds listed in table 2 were prepared according to the steps similar to the route 1 of preparation Embodiment 1, except that the boric acid derivatives in the following table were used as the raw material in step 8 instead of the raw material 1A to give the corresponding compounds.

TABLE 2

| Product identifier | Product structure | Chemical structure and identifier of raw material | Product LCMS m/z: [M + H] | $^1$H NMR of product |
|---|---|---|---|---|
| Embodiment 13 | | 13J | 369.1 | $^1$H NMR (400 MHz, CD$_3$OD) δ = 9.23 (d, J = 6.0 Hz, 1 H), 8.89 (d, J = 2.0 Hz, 1 H) 8.81 (d, J = 1.8 Hz, 1 H), 8.32 (d, J = 8.8 Hz, 1 H), 8.04 (d, J = 6.0 Hz, 1 H), 7.80-7.86 (m, 2 H), 7.36-7.41 (m, 3 H), 6.89-6.95 (m, 1 H), 6.89-6.95 (m, 2 H). |

TABLE 2-continued

| Product identifier | Product structure | Chemical structure and identifier of raw material | Product LCMS m/z: [M + H] | ¹H NMR of product |
|---|---|---|---|---|
| Embodiment 14 | | 14K | 369.2 | ¹H NMR (400 MHz, CD$_3$OD) δ = 9.29 (s, 1 H), 9.11 (s, 1 H), 8.79 (d, J = 1.8 Hz, 1 H), 8.70 (d, J = 1.8 Hz, 1 H), 7.75-7.87 (m, 3 H), 7.22-7.32 (m, 2 H), 6.78-6.85 (m, 2 H). |
| Embodiment 15 | | 2B | 382.0 | ¹H NMR (400 MHz, DMSO-d$_6$) δ = 9.02 (d, J = 1.8 Hz, 1H), 8.87 (d, J = 1.8 Hz, 1H), 7.73-7.59 (m, 2H), 7.42-7.30 (m, 4H), 7.11 (d, J = 16.4 Hz, 2H), 2.40-2.33 (m, 3H). |
| Embodiment 16 | | 16 L | 384.2 | ¹H NMR (400 MHz, DMSO-d$_6$) δ = 9.00-8.95 (m, 2H), 8.83 (d, J = 1.8 Hz, 1H), 7.56 (d, J = 1.8 Hz, 1H), 7.51-7.42 (m, 3H), 7.41-7.30 (m, 3H), 7.03 (t, J = 8.8 Hz, 2H), 6.80 (s, 2H). |
| Embodiment 17 | | 17 M | 386.1 | ¹H NMR (400 MHz, DMSO-d$_6$) δ = 8.96 (d, J = 2.0 Hz, 1H), 8.90 (dd, J = 1.8, 4.2 Hz, 1H), 8.83 (d, J = 2.0 Hz, 1H), 8.26 (d, J = 8.6 Hz, 1H), 7.60-7.52 (m, 4H), 7.48 (dd, J = 1.6, 11.8 Hz, 1H), 7.41-7.32 (m, 2H), 7.02 (t, J = 8.8 Hz, 2H). |

TABLE 2-continued

| Product identifier | Product structure | Chemical structure and identifier of raw material | Product LCMS m/z: [M + H] | ¹H NMR of product |
|---|---|---|---|---|
| Embodiment 18 | | 18 N | 368.3 | ¹H NMR (400 MHz, DMSO-d₆) δ 9.37 (s, 1H), 8.99 (d, J = 1.8 Hz, 1H), 8.86 (d, J = 1.8 Hz, 1 H), 7.97-8.00 (m, 2 H), 7.29-7.41 (m, 4 H), 7.05 (t, J = 8.8 Hz, 3 H). |
| Embodiment 19 | | 19 O | 357.3 | ¹H NMR (400 MHz, DMSO-d₆) δ = 9.00 (d, J = 1.8 Hz, 1H), 8.85 (d, J = 1.8 Hz, 1H), 8.35 (s, 1H), 7.85 (s, 1H), 7.55 (br d, J = 6.8 Hz, 3H), 7.50-7.41 (m, 3H), 7.10 (t, J = 8.8 Hz, 2H), 7.03 (dd, J = 1.6, 9.2 Hz, 1H). |
| Embodiment 20 | | 20 P | 357.1 | ¹H NMR (400 MHz, CDCl₃) δ = 8.86 (d, J = 1.8 Hz, 1H), 8.62 (d, J = 1.8 Hz, 1H), 7.95 (s, 1H), 7.54 (s, 1H), 7.37 (d, J = 8.8 Hz, 1H), 7.27 (dd, J = 5.6, 8.8 Hz, 2H), 7.17 (s, 1H), 6.79 (t, J = 8.8 Hz, 2H), 6.06 (br s, 2H). |
| Embodiment 21 | | 21Q | 391.1 | ¹H NMR (400 MHz, DMSO-d₆) δ = 13.54 (br s, 1H), 8.96 (d, J = 2.0 Hz, 1H), 8.82 (d, J = 2.0 Hz, 1H), 8.15-8.06 (m, 1H), 7.50-7.44 (m, 3H), 7.41-7.34 (m, 2H), 7.28 (d, J = 1.2 Hz, 1H), 7.07-6.99 (m, 2H). |

TABLE 2-continued

| Product identifier | Product structure | Chemical structure and identifier of raw material | Product LCMS m/z: [M + H] | $^1$H NMR of product |
|---|---|---|---|---|
| Embodiment 22 | | 22 R | 391.1 | $^1$H NMR (400 MHz, DMSO-d$_6$) δ = 13.24 (br s, 1H), 8.96 (d, J = 1.8 Hz, 1H), 8.81 (d, J = 1.8 Hz, 1H), 7.46-7.38 (m, 4H), 7.34 (dd, J = 5.8, 8.6 Hz, 2H), 7.20 (d, J = 8.6 Hz, 1H), 7.01 (t, J = 8.8 Hz, 2H). |
| Embodiment 23 | | 23S | 374.1 | $^1$H NMR (400 MHz, DMSO-d$_6$) δ = ppm 9.37 (s, 1 H), 8.99 (d, J = 1.8 Hz, 1 H), 8.86 (d, J = 1.8 Hz, 1 H), 7.97-8.00 (m, 2 H), 7.29-7.41 (m, 4 H), 7.05 (t, J = 8.8 Hz, 3 H). |

Embodiment 24

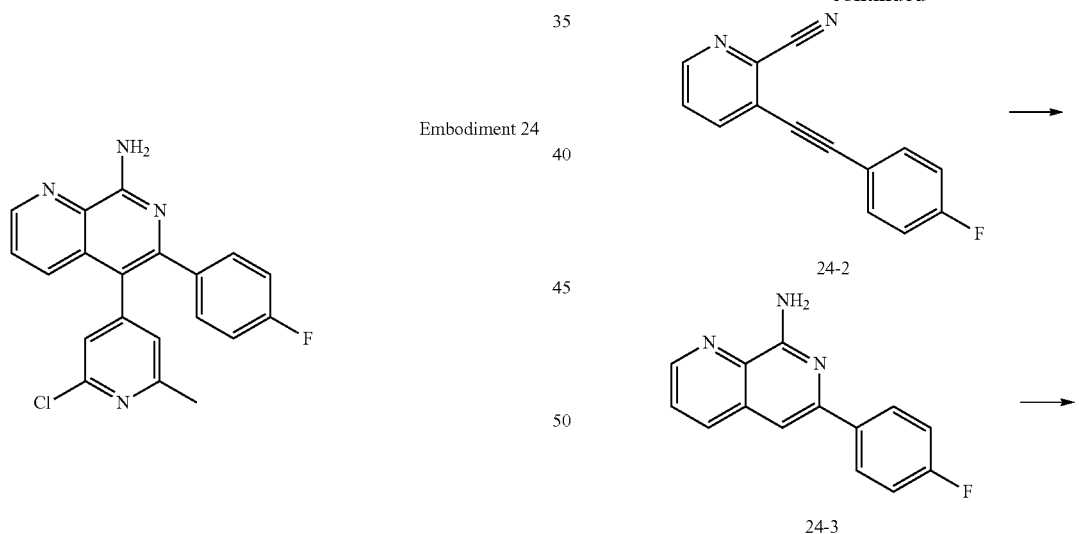

Synthesis Embodiment 24 used (24-1) as the initial raw material, the detailed synthesis route was as follows:

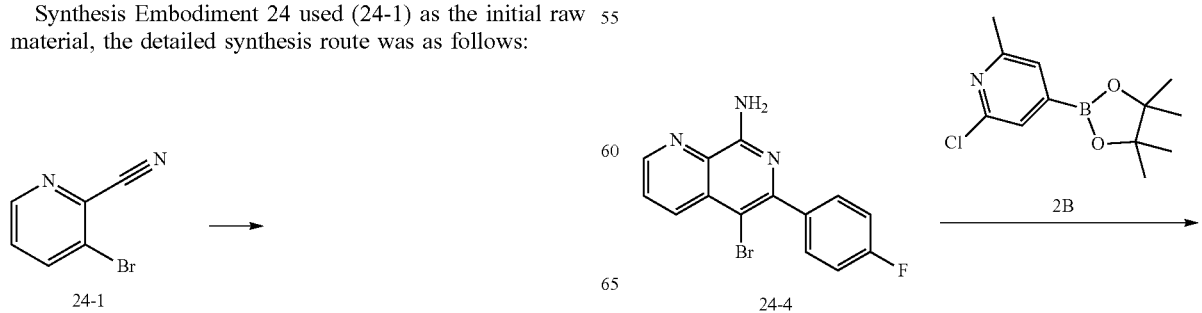

-continued

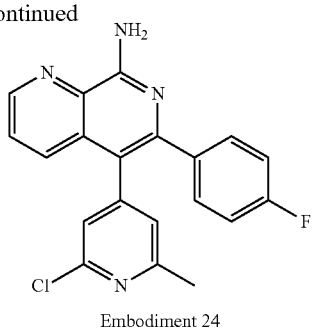

Embodiment 24

Step 1 (Synthesis of Compound 24-2)

Compound 24-1 (1.0 g, 5.46 mmol, 1 eq), triethylamine (1.66 g, 16.39 mmol, 2.28 mL, 3.0 eq), cuprous iodide (208.14 mg, 1.09 mmol, 0.2 eq) and bis(triphenylphosphino)palladium dichloride (767.08 mg, 1.09 mmol, 0.2 eq) were added into a solution of p-fluorophenylacetylene (722.04 mg, 6.01 mmol, 687.65 µL, 1.1 eq) in N,N-dimethylformamide (20 mL), the reaction mixture was purged with nitrogen for several times and then heated to 90° C. and stirred for 3 hours. LCMS showed that the raw materials disappeared and the product formed. Water (50 mL) was added into the mixture, then the mixture was extracted with ethyl acetate (50 mL*2). The organic phases were combined and washed with water (30 mL*2) and saturated brine (30 mL), dried over sodium sulfate, filtered, concentrated and purified by column chromatography (SiO$_2$, PE/ethyl acetate=5/1) to give compound 24-2.

Relevant characterization data: LCMS m/z: 223.1 [M+H]+.

Step 2 (Synthesis of Compound 24-3)

Aqueous ammonia (18.59 g, 148.50 mmol, 20.43 mL, 28% by weight, 30 eq) and potassium carbonate (1.37 g, 9.90 mmol, 2.0 eq) were added into a solution of compound 24-2 (1.1 g, 4.95 mmol, 1 eq) in N,N-dimethylformamide (10 mL), and the mixture was heated to 80° C. and stirred for 15 hours. LCMS showed the product formed. Water (50 mL) was added into the mixture, then the mixture was extracted with ethyl acetate (15 mL*3). The combined organic phase was washed with water (20 mL*3) and saturated brine (20 mL), dried over sodium sulfate, filtered and concentrated to give a crude product of compound 24-3.

Relevant characterization data: LCMS m/z: 240.1 [M+H]+.

Step 3 (Synthesis of Compound 24-4)

N-Bromosuccinimide (818.33 mg, 4.60 mmol, 1.1 eq) was added to a solution of compound 24-3 (1.0 g, 4.18 mmol, 1 eq) in acetonitrile (5 mL) at 0° C. under nitrogen atmosphere, and the mixture was heated to 25° C. and stirred for 1 hour. LCMS showed that the raw materials disappeared and the product formed. The mixture was concentrated and diluted with water (20 mL), then extracted with ethyl acetate (15 mL*3). The combined organic phase was washed with saturated sodium sulfite (15 mL*2) solution and saturated brine (15 mL), dried over sodium sulfate, filtered, and the filtrate was concentrated to give a crude product of compound 24-4. The crude product was directly used in the next step without further purification.

Relevant characterization data: LCMS m/z: 318.0 [M+H]+.

Step 4 (Synthesis of Embodiment 24)

Compound 24-4 (200 mg, 628.65 µmol, 1 eq), potassium phosphate (400.32 mg, 1.89 mmol, 3.0 eq) and [1,1'-bis(di-tert-butylphosphino)ferrocene]palladium dichloride (81.94 mg, 125.73 µmol, 0.2 eq) were added to a solution of compound 2B (159.38 mg, 628.65 µmol, 1.0 eq) in dioxane (10 mL) and water (2 mL), the mixture was heated to 90° C. under nitrogen atmosphere and stirred for 1 hour. LCMS showed that the raw materials disappeared and the product formed. The mixture was filtered and the filtrate was concentrated. The residue was separated and purified by preparative TLC plate (SiO$_2$, PE/ethyl acetate=2/1) to give Embodiment 24.

Relevant characterization data: LCMS m/z: 365.1 [M+H]+;

$^1$H NMR (400 MHz, CDCl$_3$) δ=8.73 (d, J=3.0 Hz, 1H), 7.74 (d, J=8.0 Hz, 1H), 7.46 (dd, J=4.2, 8.6 Hz, 1H), 7.29-7.14 (m, 2H), 6.98-6.83 (m, 3H), 6.79 (s, 1H), 6.14 (br s, 2H), 2.34 (s, 3H).

Embodiment 25

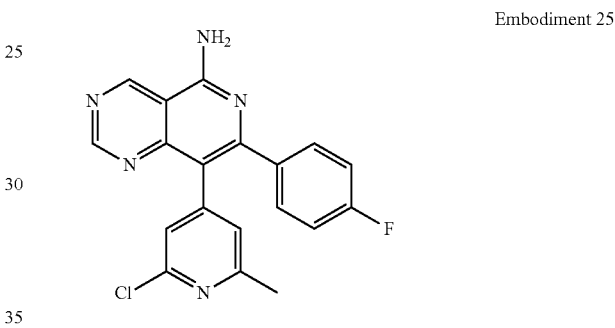

Embodiment 25

Embodiment 25 was prepared according to the steps similar to preparation Embodiment 24, except that raw material 4-chloro-5-cyanopyrimidine was used in step 1 instead of raw material 24-1 to give the corresponding Embodiment 25.

Relevant characterization data: LCMS m/z: 366.2 [M+H]+;

$^1$H NMR (400 MHz, DMSO-d$_6$) δ=9.80 (s, 1H), 9.26 (s, 1H), 7.99 (s, 2H), 7.37 (dd, J=5.6, 8.8 Hz, 2H), 7.15 (t, J=9.2 Hz, 2H), 7.11 (s, 1H), 7.06 (s, 1H), 2.36 (s, 3H).

Embodiment 26

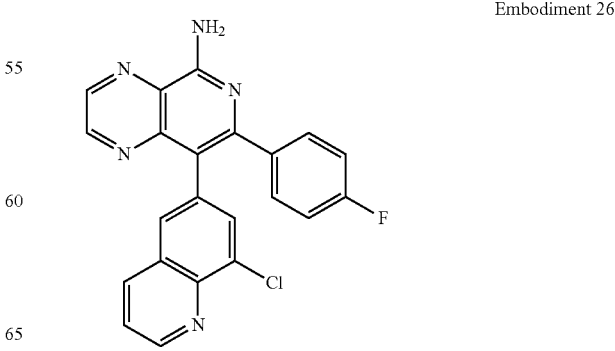

Embodiment 26

Synthesis Embodiment 26 used (1-8) as the raw material, the detailed synthesis route was as follows:

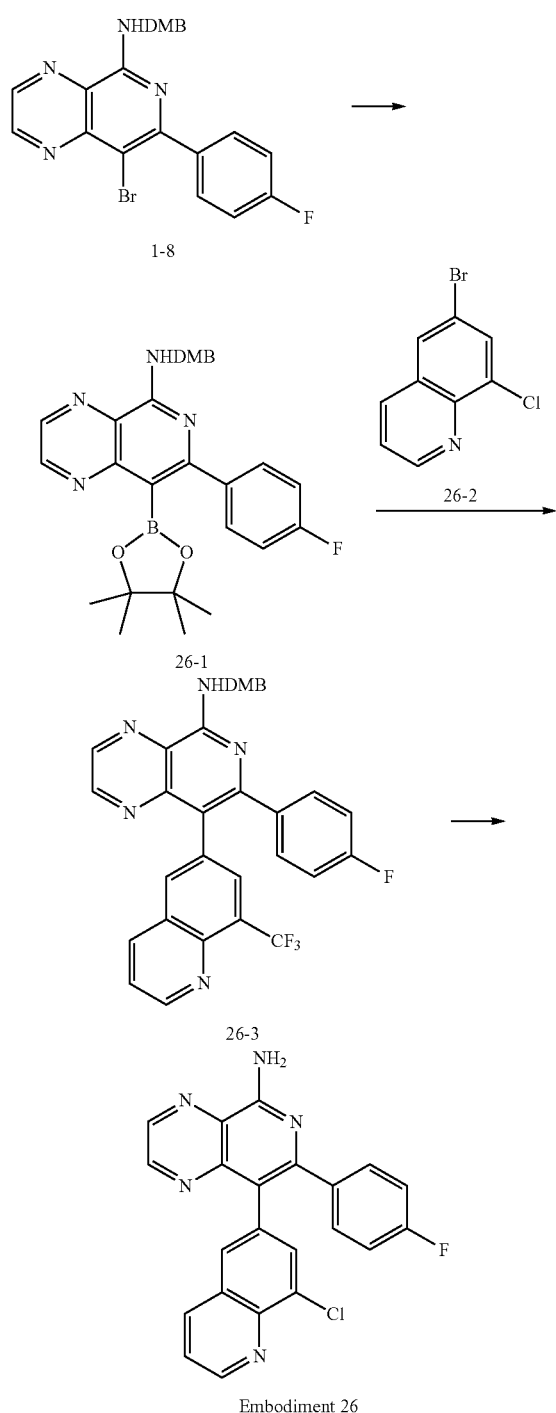

Step 1 (Synthesis of Compound 26-1)

Under nitrogen protection, a solution of compound 1-8 (0.9 g, 1.92 mmol, 1 eq), pinacol borate (2.43 g, 9.59 mmol, 5 eq), Pd(dbcp)$_2$Cl$_2$ (124.99 mg, 191.77 μmol, 0.1 eq) and potassium acetate (564.63 mg, 5.75 mmol, 3 eq) in dioxane (20 mL) was stirred at 90° C. for 30 minutes. LCMS showed that the raw materials disappeared and the product formed. The reaction mixture was cooled to room temperature, filtered, and the filtrate was evaporated to dryness. The crude product was separated and purified by column chromatography (PE/ethyl acetate=10:1 to 5:1, 100-200 mesh silica gel) to give compound 26-1.

Relevant characterization data: LCMS m/z: 517.3 [M+H]+.

Step 2 (Synthesis of Compound 26-3)

Under nitrogen protection, a solution of compound 26-1 (0.2 g, 132.58 μmol, 1 eq), compound 26-2 (64.30 mg, 265.16 μmol, 2 eq), Pd(dbcp)$_2$Cl$_2$ (8.64 mg, 13.26 μmol, 0.1 eq) and potassium carbonate (54.97 mg, 397.74 μmol, 3 eq) in dioxane (2 mL) and water (0.4 mL) was stirred at 90° C. for 30 minutes. LCMS showed that the raw materials disappeared and the product formed. The reaction mixture was cooled to room temperature, filtered, and the filtrate was evaporated to dryness. The crude product was separated and purified by column chromatography (PE/ethyl acetate=5/1 to 1/1,100-200 mesh silica gel) to give Compound 26-3.

Relevant characterization data: LCMS m/z: 552.2 [M+H]+.

Step 3 (Synthesis of Embodiment 26)

A solution of compound 26-3 (0.06 g, 103.63 μmol, 1 eq) in trifluoroacetic acid (3 mL) was stirred at 70° C. for 30 minutes. LCMS showed that the raw materials disappeared and the product formed. The reaction mixture was concentrated and evaporated to dryness, diluted with water (10 mL), adjusted to pH 9 with saturated sodium bicarbonate solution, extracted with ethyl acetate (15 mL*3). The combined organic phase was washed with saturated brine (15 mL*2), dried over anhydrous sodium sulfate, filtered and evaporated to dryness. The crude product was purified by preparative thin layer chromatography (PE/ethyl acetate=1/1) to give Embodiment 26.

Relevant characterization data: LCMS m/z: 402.1 [M+H]+;

$^1$H NMR (400 MHz, DMSO-d$_6$) δ=9.02-8.97 (m, 2H), 8.85 (d, J=2.0 Hz, 1H), 8.31-8.26 (m, 1H), 7.84 (d, J=1.8 Hz, 1H), 7.72 (d, J=1.8 Hz, 1H), 7.62-7.57 (m, 3H), 7.39 (dd, J=5.6, 8.8 Hz, 2H), 7.05 (t, J=9.0 Hz, 2H).

Embodiment 27

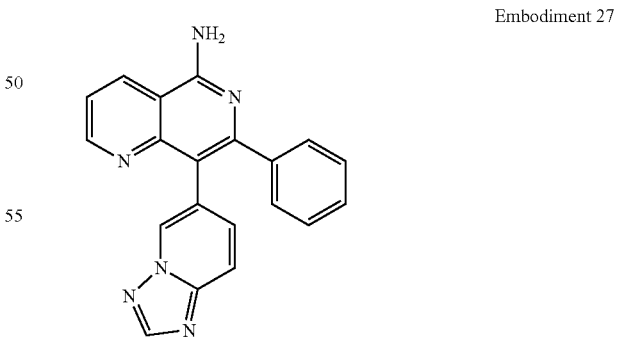

Embodiment 27

Embodiment 27 was prepared according to the steps similar to preparation Embodiment 24, except that the raw material 24-1 was replaced by 2-bromo-3-cyanopyridine in step 1, and p-fluorophenylacetylene was replaced by phenylacetylene; raw material 2B was replaced by 6F in step 4 to give the corresponding Embodiment 27.

Relevant characterization data: LCMS m/z: 339.0 [M+H]+;

$^1$H NMR (400 MHz, DMSO-$d_6$) δ=8.90 (dd, J=1.2, 4.0 Hz, 1H), 8.74 (dd, J 1.2, 8.0 Hz, 1H), 8.64 (s, 1H), 8.42 (s, 1H), 7.71 (d, J=9.2 Hz, 1H), 7.55 (dd, J 4.4, 8.4 Hz, 1H), 7.47 (dd, J=1.6, 9.2 Hz, 1H), 7.42 (s, 2H), 7.37 (dd, J=2.0, 8.0 Hz, 2H), 7.25-7.17 (m, 3H).

Embodiment 28

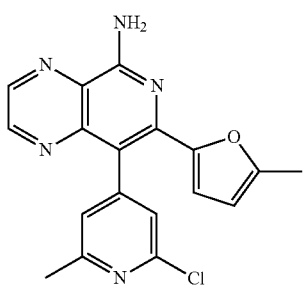

Embodiment 28

Synthesis Embodiment 28 used (28-1) as the initial raw material, the detailed synthesis route was as follows:

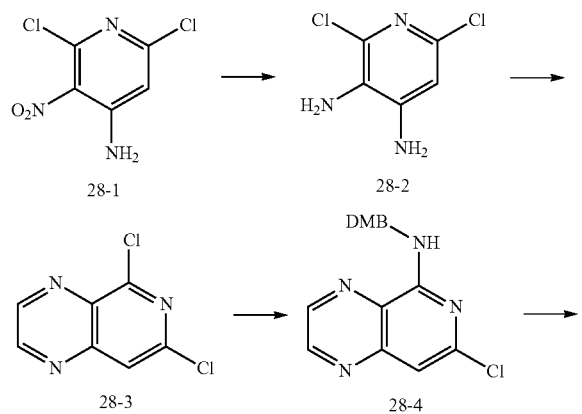

28-1 → 28-2

28-3 → 28-4

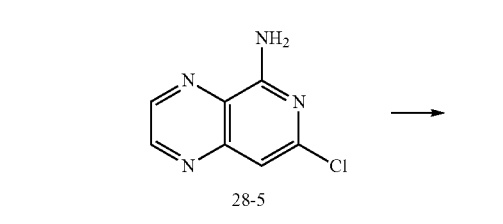

28-5 →

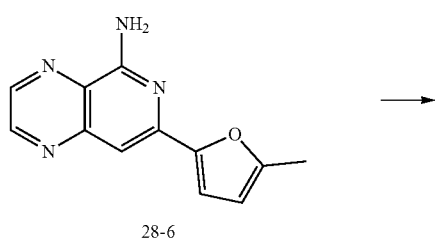

28-6

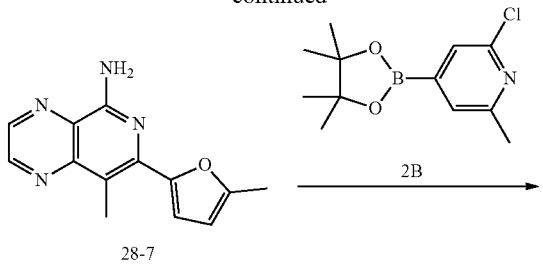

28-7

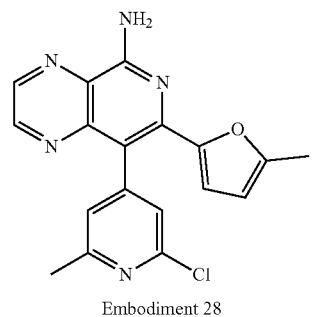

Embodiment 28

Step 1 (Synthesis of Compound 28-2)

Iron powder (6.71 g, 120.19 mmol, 5.0 eq) was added to a solution of compound 28-1 (5.00 g, 24.04 mmol, 1 eq) in ethanol (100 mL), then hydrochloric acid (36.52 g, 360.57 mmol, 35.80 mL, weight content 36%, 15 eq) was added at 0° C. The mixture was stirred at 0-15° C. for 10 minutes, then heated to 25° C., and stirred at 25° C. for 10 hours. LCMS showed that the raw materials disappeared and the product formed. The mixture was filtered, the filter cake was washed with water (15 mL*3), and the filtrates were combined. The filtrate was adjusted to pH 10 (aqueous NaOH solution, 6M), and a large amount of precipitate generated, then ethyl acetate (200 mL) was added to the mixture. The mixture was stirred at room temperature for 30 minutes, and filtered to give the filtrate. The filtrate was extracted with ethyl acetate (50 mL*4), the combined organic phase was washed with saturated brine (50 mL) and concentrated in vacuum to give compound 28-2.

Relevant characterization data: LCMS m/z: 178.1 [M+H]$^+$.

Step 2 (Synthesis of Compound 28-3)

Glyoxal (5.13 g, 35.39 mmol, 4.63 mL, 1.5 eq) was added to a solution of compound 28-2 (4.2 g, 23.59 mmol, 1 eq) in ethanol (40 mL), and the mixture was heated to 80° C. and stirred at 80° C. for 2 hours. LCMS showed that the raw materials disappeared and the product formed. A lot of yellow precipitate generated in the system, and the mixture was filtered and the filter cake was dried to give compound 28-3.

Relevant characterization data: LCMS m/z: 200.0 [M+H].

Step 3 (Synthesis of Compound 28-4)

At room temperature, 2,4-dimethoxyaniline (835.92 mg, 5.00 mmol, 753.08 μL, 1.0 eq) and N,N-diisopropylethylamine (775.36 mg, 6.00 mmol, 1.04 mL, 1.2 eq) were added to a solution of compound 28-3 (1.0 g, 5.00 mmol, 1 eq) in tetrahydrofuran (20 mL), the mixture was stirred at 25° C. for 4 hours, then heated to 66° C. and stirred for 1 hour. TLC showed the raw materials disappeared and LCMS detected the formation of the product. The mixture was concentrated to give compound 28-4.

Relevant characterization data: LCMS m/z: 331.0 [M+H].

Step 4 (Synthesis of Compound 28-5)

Compound 28-4 (500 mg, 1.51 mmol, 1 eq) was added to trifluoroacetic acid (3 mL), the system was heated to 70° C. and stirred for 3 hours. LCMS showed that the raw materials disappeared and the product formed. The mixture was quenched with saturated sodium carbonate aqueous solution (30 mL), extracted with ethyl acetate (15 mL*3). The organic phases were combined and washed with saturated brine (10 mL), dried over sodium sulfate, filtered, concentrated to give a crude product, which was purified by column (SiO$_2$, PE/ethyl acetate=3/1) to give compound 28-5.

Relevant characterization data: LCMS m/z: 181.1 [M+H].

Step 5 (Synthesis of Compound 28-6)

Compound 28-5 (200 mg, 1.11 mmol, 1 eq) was dissolved in a mixed solvent of 1,4-dioxane (5 mL) and water (1 mL), then 5-methyl-2-furanboronic acid pinacol ester (276.50 mg, 1.33 mmol, 1.2 eq), 1,1-bis(diphenylphosphino)ferrocene palladium chloride (162.07 mg, 221.49 μmol, 0.2 eq) and potassium phosphate (705.23 mg, 3.32 mmol, 3.0 eq) were added, the mixture was heated to 90° C. under nitrogen atmosphere and stirred at 90° C. for 1 hour. LCMS showed that the raw materials disappeared and the product formed. The mixture was filtered to obtain the filtrate, the filter cake was washed with ethyl acetate (15 mL*3). The filtrates were combined and concentrated to give a crude product, which was purified by column chromatography (SiO$_2$, PE/ethyl acetate=3/1) to give compound 28-6.

Relevant characterization data: LCMS m/z: 227.1 [M+H].

Step 6 (Synthesis of Compound 28-7)

N-Iodosuccinimide (59.67 mg, 265.21 μmol, 1.2 eq) was added to a solution of compound 28-6 (50 mg, 221.01 μmol, 1 eq) in acetonitrile (3 mL), and the mixture was heated to 70° C. and stirred for 1 hour. LCMS showed that the raw materials disappeared and the product formed. The mixture was concentrated to give a crude product of compound 28-7. The crude product was directly used in the next step without further purification.

Relevant characterization data: LCMS m/z: 353.0 [M+H].

Step 7 (Synthesis of Embodiment 28)

Compound 2B (60.48 mg, 238.55 μmol, 1.2 eq) was added to a mixed solvent of 1,4-dioxane (3 mL) and water (0.05 mL), followed by addition of compound 28-7 (70 mg, 198.79 μmol, 1 eq), potassium phosphate (126.59 mg, 596.37 μmol, 3.0 eq) and 1,1-bis(diphenylphosphino)ferrocene palladium chloride (29.09 mg, 39.76 μmol, 0.2 eq), the mixture was heated to 90° C. under nitrogen atmosphere and stirred for 2 hours. LCMS showed that the raw materials disappeared and the product formed. After the completion of the reaction, the mixture was filtered, the filter cake was washed with ethyl acetate (10 mL*3). The combined filtrate was concentrated and purified by column chromatography, and further purified by preparative TLC plate (PE/ethyl acetate=3/1) to give a crude product. The crude product was separated by reverse phase preparative chromatography (column: Phenomenex Gemini 150*25 mm*10 μm; Mobile phase: [water (10 mM ammonium bicarbonate)-acetonitrile]; B %: 30%-60%, 10 min) and concentrated to give Embodiment 28.

Relevant characterization data: LCMS m/z: 352.0 [M+H];

$^1$H NMR (400 MHz, DMSO-d$_6$) δ=8.92 (d, J=1.6 Hz, 1H), 8.76 (s, 1H), 7.54 (s, 2H), 7.21 (d, J=13.6 Hz, 2H), 6.43 (d, J=3.2 Hz, 1H), 6.15 (s, 1H), 2.48 (s, 3H), 2.10 (s, 3H).

Embodiment 29

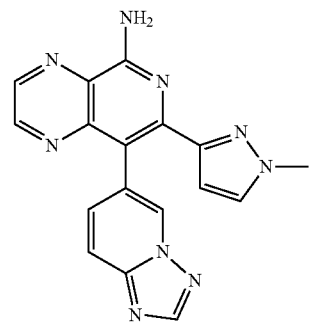

Embodiment 29

Embodiment 29 was prepared according to the steps similar to the preparation Embodiment 28 by using 28-5 as the raw material, except that the raw material 1-methylpyrazole-3-boronic acid pinacol ester was used instead of 5-methyl-2-furanboronic acid pinacol ester in step 5; the raw material 6F was used instead of the raw material 2B in step 7 to give the corresponding Embodiment 29.

Relevant characterization data: LCMS (M-1): 342.2; LCMS m/z: 344.1 [M+H]$^+$.

$^1$H NMR (400 MHz, DMSO-d$_6$) δ=8.94 (d, J=1.8 Hz, 1H), 8.80 (d, J=1.8 Hz, 1H), 8.74 (s, 1H), 8.48 (s, 1H), 7.78 (d, J=9.0 Hz, 1H), 7.55 (d, J=2.0 Hz, 1H), 7.51-7.42 (m, 3H), 6.33 (d, J=2.0 Hz, 1H), 3.61 (s, 3H).

Embodiment 30

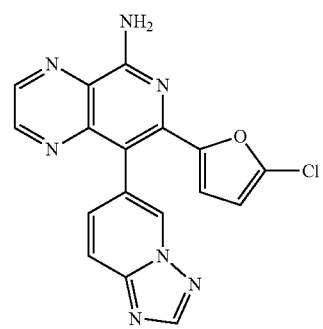

Embodiment 30

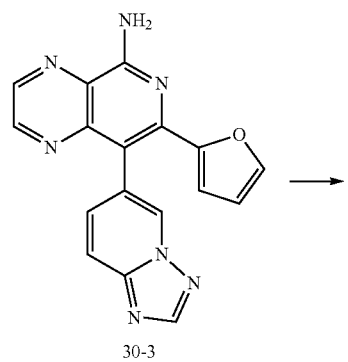

30-3

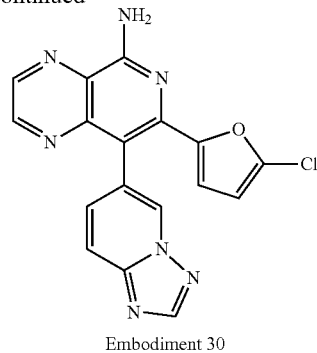

Embodiment 30

Embodiment 30 was prepared according to the steps similar to the preparation Embodiment 28, except that the raw material 2-furanboronic acid was used instead of 5-methyl-2-furanboronic acid pinacol ester in step 5; and the raw material 6F was used instead of the raw material 2B in step 7 to give the corresponding compound 30-3.

Step 8 (Synthesis of Embodiment 30)

NCS (26.13 mg, 195.72 μmol, 1.05 eq) was added to a solution of compound 30-3 (0.08 g, 186.40 μmol, 1 eq) in DMF (2 mL), and the mixture was stirred at 60° C. for 3 hours. LCMS showed a little raw material remained and the product formed. The reaction mixture was diluted with water (10 mL), extracted with ethyl acetate (15 mL*3). The combined organic phase was washed with saturated brine (15 mL*2), dried over anhydrous sodium sulfate, filtered and evaporated to dryness. The crude product was separated and purified by thin layer TLC chromatography (ethyl acetate/methanol=25/1) and high performance liquid phase preparative chromatography (column: Gemini 150*25 mm 5 μm; Mobile phase: [water (0.05% aqueous ammonia v/v)-acetonitrile]; B %: 20%-50%, 12 min) to give Embodiment 30.

Relevant characterization data: LCMS m/z: 364.1 [M+H]+;

$^1$H NMR (400 MHz, DMSO-d$_6$) δ=8.94 (d, J=2.0 Hz, 2H), 8.81 (d, J=1.8 Hz, 1H), 8.53 (s, 1H), 7.90 (d, J=9.2 Hz, 1H), 7.63 (s, 2H), 7.57 (d, J=9.0 Hz, 1H), 6.52-6.46 (m, 2H).

Embodiment 31

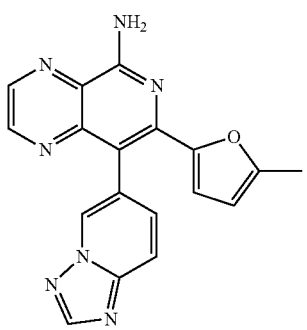

Embodiment 31

Embodiment 31 was prepared according to the steps similar to the preparation Embodiment 28 by using 28-7 as raw material, except that the raw material 6F was used in step 7 instead of raw material 2B to give the corresponding Embodiment 31.

Relevant characterization data: LCMS m/z: 344.2 [M+H];

$^1$H NMR (400 MHz, DMSO-d$_6$) δ=8.89 (br d, J=12.4 Hz, 2H), 8.76 (s, 1H), 8.52 (s, 1H), 7.87 (br d, J=8.8 Hz, 1H), 7.59-7.47 (m, 3H), 6.39 (s, 1H), 6.09 (s, 1H), 2.00 (s, 3H).

Embodiment 32

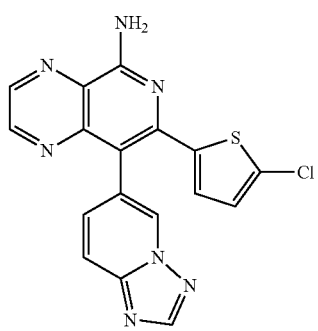

Embodiment 32

Embodiment 32 was prepared according to the steps similar to the preparation Embodiment 28 by using 28-5 as the raw material, except that the raw material 5-chlorothiophene-2-boronic acid was used in step 5 instead of 5-methyl-2-furanboronic acid pinacol ester; the raw material 6F was used in step 7 instead of the raw material 2B to give the corresponding Embodiment 32.

Relevant characterization data: LCMS m/z: 380.1 [M+H];

$^1$H NMR (400 MHz, DMSO-d$_6$) δ=9.02 (s, 1H), 8.93 (d, J=1.8 Hz, 1H), 8.80 (d, J=1.8 Hz, 1H), 8.59 (s, 1H), 7.98 (d, J=9.0 Hz, 1H), 7.69-7.56 (m, 3H), 6.91 (d, J=4.0 Hz, 1H), 6.45 (d, J=4.0 Hz, 1H).

Embodiment 33

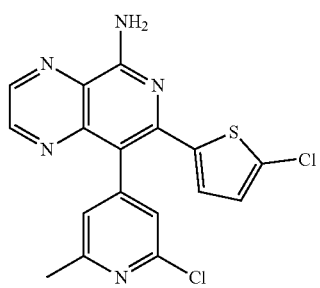

Embodiment 33

Embodiment 33 was prepared according to the steps similar to the preparation Embodiment 28, except that the raw material 5-chlorothiophene-2-boronic acid was used in step 5 instead of 5-methyl-2-furanboronic acid pinacol ester to give the corresponding embodiment 33.

Relevant characterization data: LCMS m/z: 388.0 [M+H];

$^1$H NMR (400 MHz, DMSO-d$_6$) δ=8.94 (d, J=1.8 Hz, 1H), 8.79 (d, J=2.0 Hz, 1H), 7.62 (s, 2H), 7.32 (d, J=18.8 Hz, 2H), 6.96 (d, J=4.0 Hz, 1H), 6.30 (d, J 4.2 Hz, 1H), 3.30 (s, 3H).

Embodiment 34

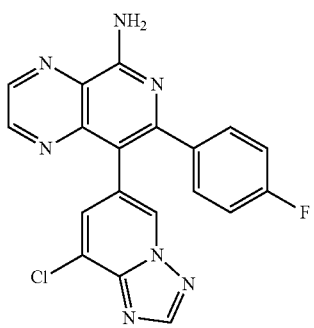

Embodiment 34

Embodiment 34 was prepared according to the steps similar to the preparation Embodiment 26, except that raw material 34-3 was used in step 2 instead of raw material 26-2 to give the corresponding Embodiment 34.

Relevant characterization data: LCMS m/z: 392.1 [M+H]; $^1$H NMR (400 MHz, CDCl$_3$) δ=8.94 (d, J=1.8 Hz, 1H), 8.82-8.71 (m, 1H), 8.44-8.30 (m, 2H), 7.51 (d, J=1.2 Hz, 1H), 7.41 (dd, J=5.6, 8.8 Hz, 2H), 6.99 (t, J 8.8 Hz, 2H), 6.20 (br s, 2H).

Biological Test Data

Experimental Example 1: In Vitro Activity Test Experiment of the Compounds of the Present Disclosure Human Adenosine $A_{2a}$ Receptor Calcium Flow Detection Experiment Cell Source:

$A_{2a}$ stable cell line was constructed by Shanghai Wuxi Apptec, and the host cell was CHO.

Test Kit:

Fluo-4 Direct kit (Invitrogen, article number: F10471). After the fluorescence detection reagent (specifically binding to calcium ions and causing an increase of fluorescence signal) in the kit was incubated with the cells for an appropriate time, the compound was added to stimulate the cells and induced changes in intracellular calcium flow, thus causing the changes in fluorescence signal, which can reflect the intensity of the agonistic or inhibiting activity of the compounds.

Cell Culture Medium:

F12+10% fetal bovine serum+geneticin 300 μg/mL+blasticidin 2 μg/mL

Compound Dilution Buffer:

Hanks balanced salt buffer (Invitrogen)+20 mM HEPES, which was prepared before each use Agonist:

NECA (Sigma-E2387)

Reference Compound (Antagonist):

CGS-15943 (Sigma-C199)

Dilution of the Compounds:

The compounds to be tested were dissolved in DMSO to prepare a 10 mM mother liquor. The test compound was diluted to 0.2 mM with DMSO, and the reference compound CGS-15943 was diluted to 0.015 mM with DMSO. Then a 10-point 3-fold serial dilution was performed with ECHO, then 900 nL of the dilutions was transferred to a compound plate (Greiner-781280), and 30 μL of the compound dilution buffer was added. The final initial concentration of the compounds to be tested was 1 μM and that of CGS-15943 was 0.075 μM.

Determination Method:

Cell Preparation:

Frozen A2A cells were suspended to 1×10$^6$ cells/mL with the culture medium after resuscitation, seeded with 20 μL/well into a 384-well polylysine coated cell plate (Greiner-781946), then incubated under 5% CO$_2$ at 37° C. overnight.

The cell plate prepared the day before was taken out from the incubator, 20 μL 2×Fluo-4 Direct™ buffer was added into each cell, then incubated under 5% CO$_2$ at 37° C. in an incubator for 50 minutes, and was allowed to stand at room temperature for 10 minutes.

Determination of EC80 of Agonist NECA;

Dilution of the agonist NECA: NECA with an initial concentration of 0.15 mM was 3-fold serially diluted with Echo to prepare 10 dilutions, and then 900 nL of the dilutions was transferred to the corresponding compound plate; then 30 μL of the compound dilution buffer was added into the corresponding compound plate. The final initial concentration was 750 nM.

FLIPR instrument and software were performed according to the set program, 10 μL of the compound dilution buffer was added into the cell plate, and the fluorescence signal was read. 10 μL of the agonist reference compound with a predetermined concentration was added to the cell plate and the fluorescence signal was read. After reading, the data were exported by "Max-Min" and "Read 90 to Maximum allowed" methods in the software, the EC80 on $A_{2A}$ cell line was calculated, and 6×EC80 concentration of agonist was prepared. The agonist reference compound with a concentration of 6×EC80 was prepared with buffer salt solution, and 30 μL/well was aliquoted into the corresponding compound plate for later use.

Determination of IC$_{50}$ of the Compounds to be Tested:

FLIPR instrument and software were performed according to the set program, 10 μL of test compounds and reference compound with a predetermined concentration was added into the cell plate, and the fluorescence signal was read. 10 μL of the agonist reference compound with a concentration of 6×EC80 was added into the cell plate and the fluorescence signal was read. For the agonist detection of the compounds, the data were exported by "Max-Min" and "Read 1 to 90" methods in the software. For the antagonist detection of the compounds, the data were exported by "Max-Min" and "Read 90 to Maximum allowed" methods in the software. The data were analyzed by GraphPad Prism 5.0 and the IC$_{50}$ value of the test compounds was calculated.

TABLE 3 the result of in vitro screening test results of the compounds of the present disclosure

| Embodiment | IC$_{50}$ value (nM) |
|---|---|
| Embodiment 1 | 4.77 |
| Embodiment 2 | 1.73 |
| Embodiment 3 | 9.46 |
| Embodiment 4 | 0.92 |
| Embodiment 5 | 27.8 |
| Embodiment 6 | 1.14 |
| Embodiment 7 | 31.37 |
| Embodiment 8 | 26.77 |
| Embodiment 9 | 15.62 |
| Embodiment 10 | 9.2 |

TABLE 3-continued the result of in vitro screening test results
of the compounds of the present disclosure

| Embodiment | $IC_{50}$ value (nM) |
|---|---|
| Embodiment 11 | 1.79 |
| Embodiment 12 | 1.56 |
| Embodiment 13 | 9.4 |
| Embodiment 14 | 0.76 |
| Embodiment 15 | 3.84 |
| Embodiment 16 | 6.1 |
| Embodiment 17 | 0.8 |
| Embodiment 18 | 78.8 |
| Embodiment 19 | 0.54 |
| Embodiment 20 | 3.32 |
| Embodiment 21 | 0.82 |
| Embodiment 22 | 38 |
| Embodiment 23 | 0.95 |
| Embodiment 24 | 5.52 |
| Embodiment 25 | 0.89 |
| Embodiment 26 | 0.92 |
| Embodiment 27 | 0.56 |
| Embodiment 28 | 1.03 |
| Embodiment 29 | 3.18 |
| Embodiment 30 | 0.35 |
| Embodiment 31 | 0.58 |
| Embodiment 32 | 1.8 |
| Embodiment 33 | 24 |
| Embodiment 34 | 1.04 |

Conclusion: as shown in Table 3, the compounds of the present disclosure exhibit excellent adenosine $A_{2A}$ receptor antagonistic activity.

Experimental Example 2: Pharmacokinetic Evaluation

Experimental materials: Balb/C mice (female, 15-30 g, 7-9 weeks old, Shanghai Linchang) were used.

Experimental method: The pharmacokinetic characteristics of the compound after intravenous injection and oral administration were tested on rodents by standard scheme, in the experiment, the candidate compounds were prepared into clear solutions and administrated to mice by single intravenous injection and single oral administration. Intravenous injection (IV) menstruum was a mixed solvent of 5% DMSO/5% polyethylene glycol hydroxystearate/90% water, and oral (PO) menstruum was a mixed solvent of 1% Tween 80, 9% PEG400 and 90% water (pH=3). The whole blood sample within 48 hours was collected, centrifuged at 3000 g at 4° C. for 15 minutes, and the supernatant was separated to obtain the plasma sample. An acetonitrile solution containing internal standard with a volume of 20 times that of the plasma sample was added to precipitate protein, the supernatant was centrifuged and an equal volume of water was added, then the supernatant was taken for injection. The blood drug concentration was quantitatively analyzed by LC-MS/MS analysis method, and the pharmacokinetic parameters such as peak concentration, peak time, clearance rate, half-life, area under the drug concentration-time curve, bioavailability, etc. were calculated.

TABLE 4

Parameters of PK in plasma of the embodiment compounds

| Candidate compound (compound prepared in each embodiment) | Clearance rate (mL/min/kg) | Half-life $T_{1/2}$ (h) | Concentration integral AUC (nM · hr) | Bioavailability F (%) |
|---|---|---|---|---|
| Embodiment 1 | 16.5 | 0.60 | 16746 | 57.6 |
| Embodiment 2 | 17.1 | 0.78 | 20262 | 76.2 |
| Embodiment 3 | 18.1 | 1.39 | 15743 | 69.0 |
| embodiment 6 | 5.87 | 0.82 | 24050 | 30.4 |
| Embodiment 12 | 1.72 | 3.28 | 258992 | 95.4 |

Conclusion: The compounds of the present disclosure can obviously improve the pharmacokinetics parameters in the mice.

Experimental Example 3: Pharmacodynamic Test of the Compounds of the Present Disclosure In Vivo Experimental materials: BALB/C mice (female); mouse colon cancer CT26 cells (Typical Culture Preservation Commission cell bank, Chinese Academy of Sciences) were cultured in vitro in monolayer with RPMI-1640 medium containing 10% fetal bovine serum in a 37° C., 5% $CO_2$ incubator. Trypsin-EDTA was used for routine digestion and passage. When the cells were in exponential growth phase and the saturation was 80%-90%, the cells were collected and counted.

Compound preparation: Embodiment 19 was weighted and added into the menstruum (10% PEG400+90% (10% Cremophor aqueous solution)) to prepare samples of 2.5 mg/mL, 5 mg/mL and 10 mg/mL respectively. 72 μL CS1003 (PD-1 antibody) solution (25 mg/mL) was taken and 1.728 mL Dulbecco's phosphate buffer (DPBS) was added to prepare a 1 mg/mL solution, then 16.2 mL DPBS was added to prepare a 0.1 mg/mL clear solution.

Experimental operation: the cells were resuspended in Dulbecco's phosphate buffer at a density of $3 \times 10^6$ cells/mL. 0.1 mL DPBS (containing $3 \times 10^5$ CT26 cells) was subcutaneously inoculated on the right back of each mouse. On the day of inoculation, the mice were randomly divided into groups with 9 mice each group according to the weight of the mice, then administration was started and continued for 20 days. During the whole experiment, the animals were weighed and the animal's health was monitored every day, in case of any special situation, the person in charge of the relevant project would be informed in time and the corresponding records would be made. Tumor diameter was measured twice a week with a vernier caliper. The calculation formula of the tumor volume was: $V=0.5 \times a \times b^2$, wherein a and b represent the long and short diameters of the tumor respectively.

TABLE 5

Dosage regimen for in vivo pharmacodynamic test of the compounds of the present disclosure

| Group | Candidate drug | Route of administration | Dosage (mg/kg) | Dosing volume (mL/kg) | Dosage regimen |
|---|---|---|---|---|---|
| 1 | Menstruum control | Intragastric administration | — | 10 | Once a day. |
| 2 | CS1003 | Intraperitoneal injection | 1 | 10 | Day 7, 10, 13, 16 |
| 3 | Embodiment 6 hydrochloride | Intragastric administration | 100 | 10 | Once a day. |

TABLE 5-continued

Dosage regimen for in vivo pharmacodynamic test of the compounds of the present disclosure

| Group | Candidate drug | Route of administration | Dosage (mg/kg) | Dosing volume (mL/kg) | Dosage regimen |
|---|---|---|---|---|---|
| 4 | Embodiment 6 hydrochloride of + CS1003 | Intraperitoneal injection + intragastric administration | 25 | 10 + 10 (Embodiment 6 hydrochloride) + 1 (CS1003) | Once a day + Day 7, 10, 13, 16 |
| 5 | Embodiment 6 hydrochloride + CS1003 | Intraperitoneal injection + intragastric administration | 50 | 10 + 10 (Embodiment 6 hydrochloride) + 1 (CS1003) | Once a day + Day 7, 10, 13, 16 |
| 6 | Embodiment 6 hydrochloride + CS1003 | Intraperitoneal injection + intragastric administration | 100 | 10 + 10 (Embodiment 6 hydrochloride) + 1 (CS1003) | Once a day + Day 7, 10, 13, 16 |
| 7 | Embodiment 6 hydrochloride | Intragastric administration | 50 | 10 | Twice a day. |
| 8 | Embodiment 6 hydrochloride + CS1003 | Intraperitoneal injection + intragastric administration | 50 | 10 + 10 (Embodiment 6 hydrochloride) + 1 (CS1003) | Twice a day + Day 7, 10, 13, 16 |

The antitumor effect of the compounds was evaluated by GI (%) or relative tumor proliferation rate T/C (%). Relative tumor proliferation rate T/C (%)=$V_t/V_C \times 100\%$ (Vt: average tumor volume of treatment group; Vc: average tumor volume of negative control group). Vt and VC were the data on the same day.

GI (%), tumor inhibition rate. GI (%)=$1-V_t/V_C \times 100\%$.

Statistical analysis was conducted using SPSS software based on the relative tumor volume and tumor weight at the end of the experiment. The comparison between the two groups was analyzed by t-test, and the comparison between three or more groups was analyzed by one-way ANOVA, if the variance was homogenous (F value showed no significant difference), Tukey's method was used for analysis, and if the variance was not uniform (F values had significant difference), Games-Howell method is used for inspection. P<0.05 was considered as significant difference.

On the 20th day after starting administration, the tumor volume in menstruum group reached 847.09+79.65 mm³, while the tumor volume in CS1003 (1 mg/kg) group was 487.34+109.07 mm³, with a tumor inhibition rate of 42.47% (no significant difference compared with the control group). Compared with the menstruum group, the drug combination groups can significantly inhibit the growth of transplanted tumor in vivo, and the efficacy of Embodiment 6 hydrochloride in combination with CS1003 has a positive correlation with the dose and administration frequency. The tumor volumes at the end of the experiment were 312.06+80.17 mm³, 246.48+62.57 mm³, and 233.10+59.55 mm³ for 25 mg/kg, 50 mg/kg, and 100 mg/kg of the Embodiment 6 hydrochloride combined with 1 mg/kg of CS1003, respectively; the tumor inhibition rates were 63.16%, 70.90% and 72.48% respectively (p<0.001). However, the Embodiment 6 hydrochloride (50 mg/kg) administered twice a day in combination with CS1003 showed a stronger tumor inhibition effect, the average tumor volume of this group at the end of the experiment was 142.17+40.30 mm³, and the tumor inhibition rate was 83.22% (P<0.001). Thus, the Embodiment 6 hydrochloride can significantly inhibit the growth of the homograft tumor in vivo of mouse colon cancer cell CT26 when combined with CS1003 for prophylactic administration.

The Embodiment 6 hydrochloride (50 mg/kg)+CS1003 (1 mg/kg), Embodiment 6 hydrochloride (100 mg/kg)+CS1003, and Embodiment 6 hydrochloride (50 mg/kg twice a day)+CS1003 show a significant difference compared with the Embodiment 6 hydrochloride monotherapy, wherein the P values of the three groups were 0.032, 0.023 and 0.002 respectively compared with 50 mg/kg of Embodiment 6 hydrochloride; compared with 100 mg/kg of Embodiment 6 hydrochloride, the P values of the three groups were 0.038, 0.027 and 0.002 respectively. Additionally, the Q value was calculated by using the Jin's formula. It was found that the Embodiment 6 hydrochloride (50 mg/kg) had a certain additive effect with CS1003, while Embodiment 6 hydrochloride (100 mg/kg) had a synergistic effect with CS1003.

Conclusion: the combination of the compounds of the present disclosure and CS1003 can achieve a better tumor inhibition effect, and the combination of the compounds of the present disclosure and CS1003 has synergistic effect.

Experimental Example 4: PK Test of In Vivo Efficacy of the Compounds of the Present Disclosure The experiment was conducted on the basis of experimental example 3, on the 20th day after administration, blood samples and tissues were collected from each group at different time points (0 h, 0.25 h, 0.5 h, 1 h, 2 h, 4 h, 8 h and 24 h) after administration.

TABLE 6

Pharmacokinetic parameters of each experimental group measured by the tests

| | Compound ID | Embodiment 6 hydrochloride | Embodiment 6 hydrochloride | Embodiment 6 hydrochloride | Embodiment 6 hydrochloride | Embodiment 6 hydrochloride | Embodiment 6 hydrochloride |
|---|---|---|---|---|---|---|---|
| PK | Group | 4 | 5 | 6 | 3 | 7 | 8 |
| PO | Cmax (nM) | 32200 | 57200 | 132000 | 114000 | 30100 | 47100 |
| | Tmax (h) | 0.500 | 0.250 | 0.250 | 0.250 | 0.500 | 0.500 |
| | T½ (h) | 1.09 | 1.05 | 0.655 | 0.81 | NR | 1.59 |
| | AUC0-last (nM · h) | 23500 | 70600 | 125000 | 145000 | 42000 | 77900 |

TABLE 7

The drug concentration in the tumor tissue and the biological proportion of the drug concentration in the tumor tissue and the plasma drug concentration at corresponding blood collection points in each experimental group measured by tests

| Compound ID | Embodiment 6 hydrochloride | | Embodiment 6 hydrochloride | | Embodiment 6 hydrochloride | | Embodiment 6 hydrochloride | | Embodiment 6 hydrochloride | | Embodiment 6 hydrochloride | |
|---|---|---|---|---|---|---|---|---|---|---|---|---|
| Group | 25 mpk 4 | | 50 mpk 5 | | 100 mpk 6 | | 100 mpk 3 | | 50 mpk 7 | | 50 mpk 8 | |
| Time point (h) | 1 | 4 | 1 | 4 | 1 | 4 | 1 | 4 | 1 | 4 | 1 | 4 |
| Tumor drug concentration (nM) | 3480 | 925 | 9960 | 1660 | 18700 | 3030 | 17500 | 10600 | 3690 | 901 | ND | 3020 |
| T/P* Ratio | 0.7 | 0.9 | 0.4 | 1.8 | 0.5 | 4.2 | 0.6 | 0.9 | 0.7 | 9.8 | ND | 36 |

Conclusion: The compounds of the present disclosure have sufficient exposure in plasma and tumor tissue.

What is claimed is:

1. A compound represented by formula (I) or a pharmaceutically acceptable salt thereof,

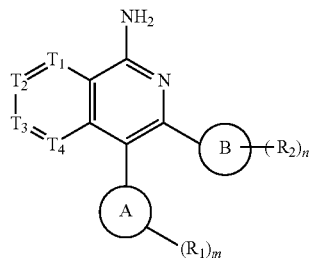

wherein,
1 or 2 of $T_1$, $T_2$, $T_3$ and $T_4$ is N, the rest are independently CH;
each of $R_1$ is independently selected from H, halogen, OH, $NH_2$ or $C_{1-3}$ alkyl optionally substituted by 1, 2 or 3 R;
each of $R_2$ is independently selected from H, halogen, OH, $NH_2$ or $C_{1-3}$ alkyl optionally substituted by 1, 2 or 3 R;
n is selected from 0, 1, 2 and 3;
m is selected from 0, 1, 2 and 3;
ring A is selected from 6-10 membered aryl and 5-10 membered heteroaryl;
ring B is selected from phenyl and 5-6 membered heteroaryl;
R is selected from F, Cl, Br, I, OH, $NH_2$ and CN;
the "hetero" in the 5-6 membered heteroaryl and 5-10 membered heteroaryl are each independently selected from N, O, S, NH, —C(═O)—, —C(═O)O— and —C(═O)NH—;
the number of the heteroatom or heteroatom group is independently selected from 1, 2, 3 and 4.

2. The compound or the pharmaceutically acceptable salt thereof according to claim 1, wherein each of $R_1$ is independently selected from H, F, Cl, Br, I, OH, $NH_2$, Me and Et, wherein the Me and Et are optionally substituted by 1, 2 or 3 R.

3. The compound or the pharmaceutically acceptable salt thereof according to claim 2, wherein each of $R_1$ is independently selected from H, F, Cl, Br, I, OH, $NH_2$, Me, $CF_3$ and Et.

4. The compound or the pharmaceutically acceptable salt thereof according to claim 1, wherein each of $R_2$ is independently selected from H, F, Cl, Br, I, OH, $NH_2$ and Me optionally substituted by 1, 2 or 3 R.

5. The compound or the pharmaceutically acceptable salt thereof according to claim 4, wherein each of $R_2$ is independently selected from F, Cl, Br, I, OH, $NH_2$ and Me.

6. The compound or the pharmaceutically acceptable salt thereof according to claim 1, wherein ring A is selected from phenyl, pyridyl, quinoxalyl, 1,2,3,4-tetrahydroquinolyl, 3,4-dihydro-2H-benzo[b][1,4]oxazinyl, benzo[d]isoxazolyl, [1,2,4]triazolo[4,3-a]pyridyl, 1H-benzo[d][1,2,3]triazolyl, cinnolinyl, quinazolinyl, quinolyl, isoquinolyl, imidazo[1,2-a]pyridyl, [1,2,4]triazolo[1,5-a]pyridyl, 1H-indazolyl and benzo[d]thiazolyl.

7. The compound or the pharmaceutically acceptable salt thereof according to claim 5, wherein the structural unit

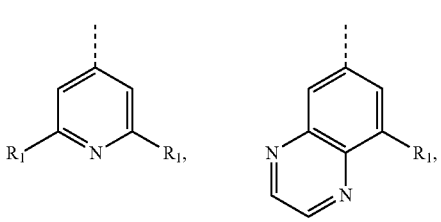

is selected from

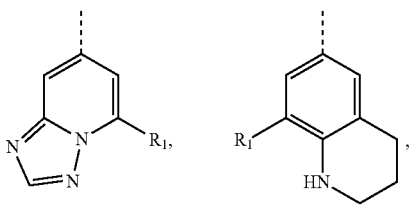

-continued
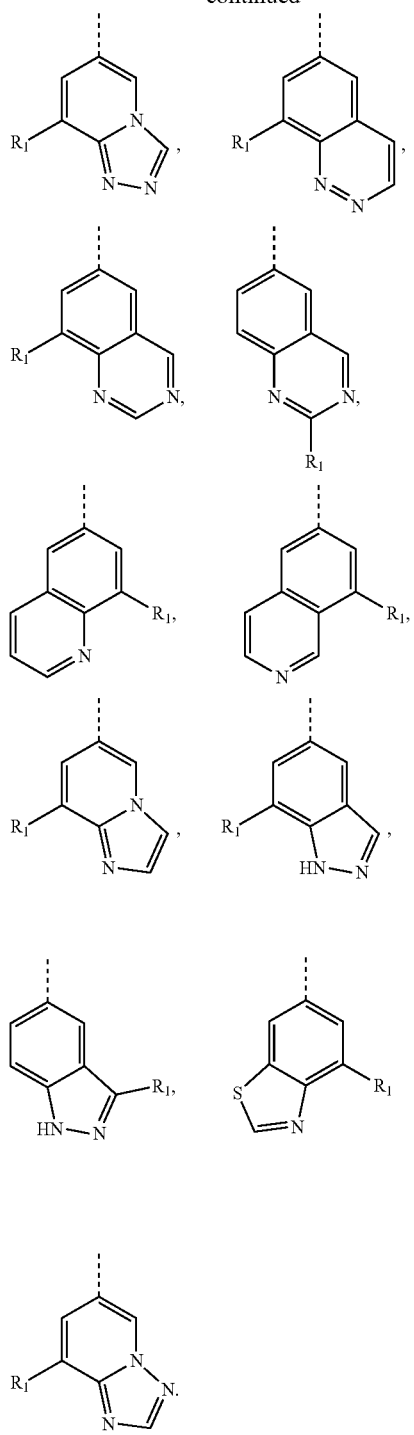
8. The compound or the pharmaceutically acceptable salt thereof according to claim 3, wherein the structural unit
is selected from
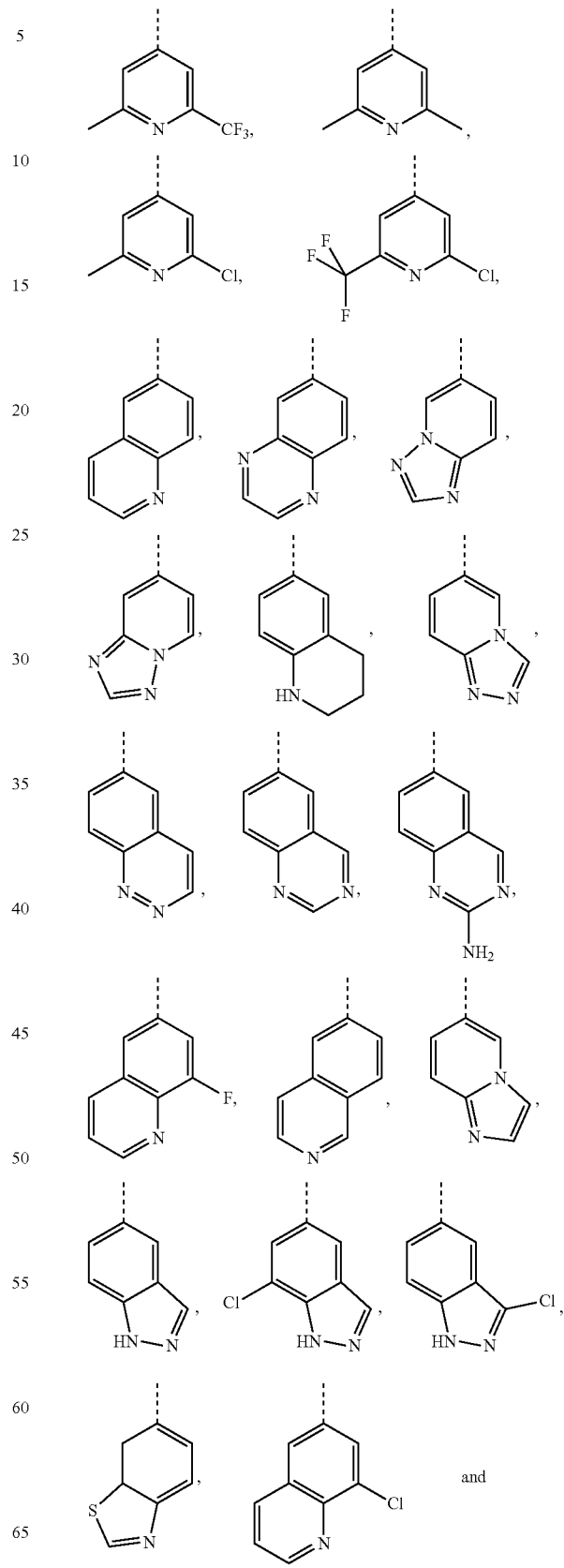
and -continued

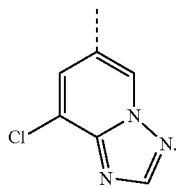

9. The compound or the pharmaceutically acceptable salt thereof according to claim 1, wherein ring B is selected from phenyl, furanyl, thienyl and pyrazolyl.

10. The compound or the pharmaceutically acceptable salt thereof according to claim 9, wherein the structural unit

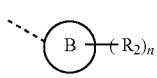

is selected from

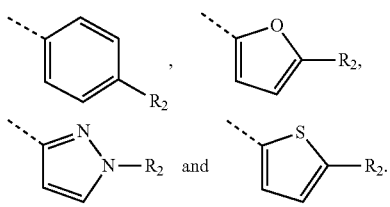

11. The compound or the pharmaceutically acceptable salt thereof according to claim 5, wherein the structural unit

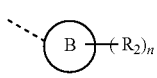

is selected from

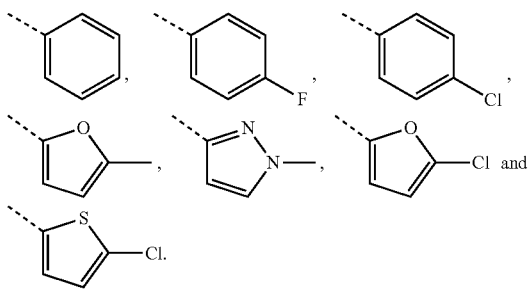

12. The compound or the pharmaceutically acceptable salt thereof according to claim 1, wherein the structural unit

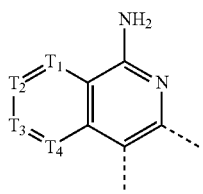

is selected from

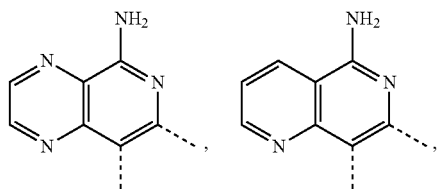

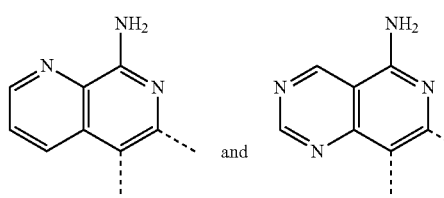

13. The compound or the pharmaceutically acceptable salt thereof according to claim 1, which is selected from the group consisting of:

(I-1)

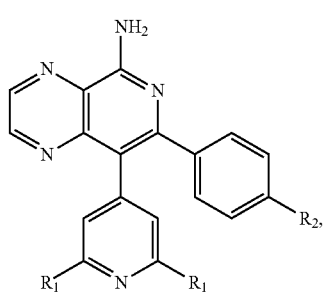

(I-2)

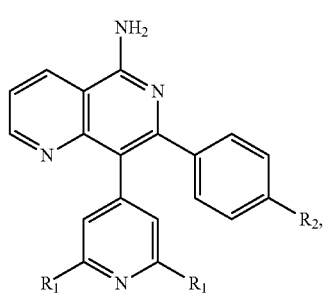

(I-3)

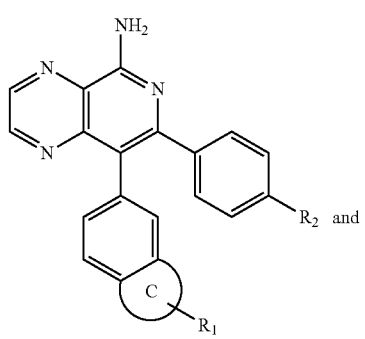

and

-continued (I-4)

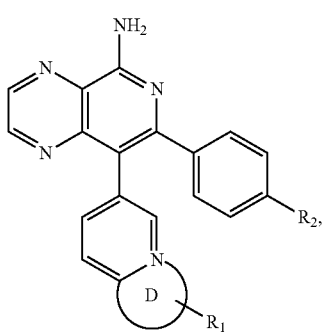

wherein,
$R_1$ and $R_2$ are as defined in claim 1;
ring C is selected from 5-6 membered heteroaryl and 5-6 membered heterocycloalkyl;
ring D is 5-6 membered heteroaryl;
the "hetero" in the 5-6 membered heteroaryl is selected from N, S and NH;
the "hetero" in the 5-6 membered heterocycloalkyl is NH;
the number of the heteroatom or heteroatom group is independently selected from 1, 2, 3 and 4.

14. The compound or the pharmaceutically acceptable salt thereof according to claim 13, wherein the structural unit

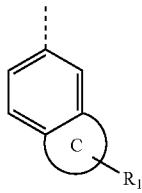

is selected from

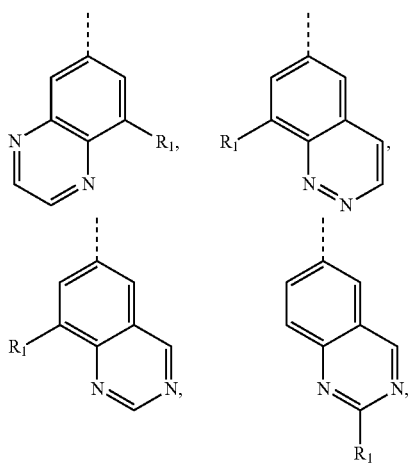

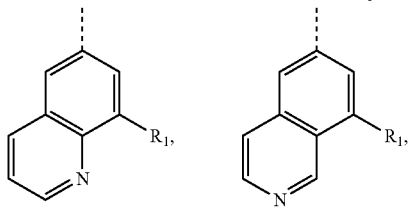

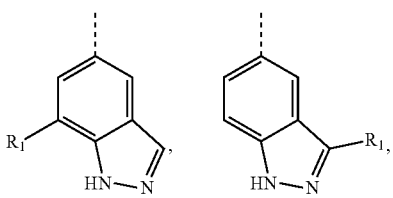

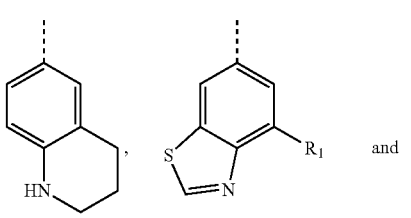

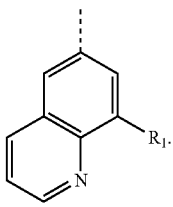

15. The compound or the pharmaceutically acceptable salt thereof according to claim 13, wherein the structural unit

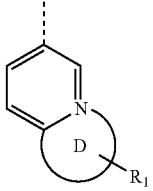

is selected from

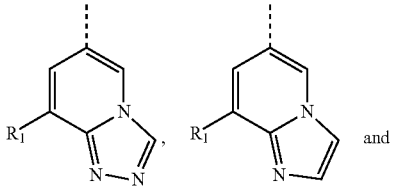

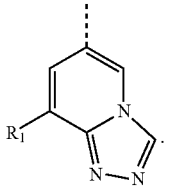

16. A compound or a pharmaceutically acceptable salt thereof, wherein the compound is selected from the group consisting of:
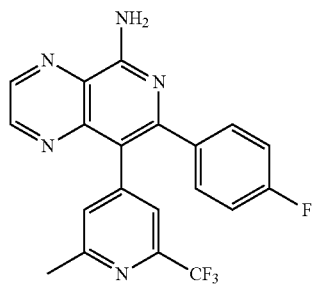
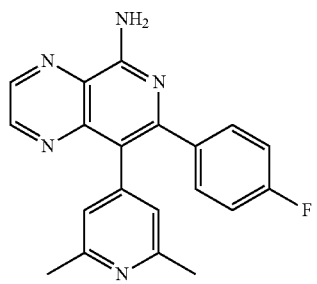
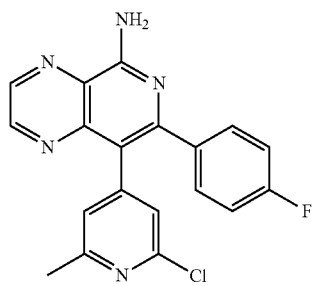
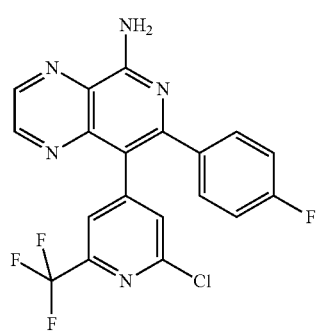
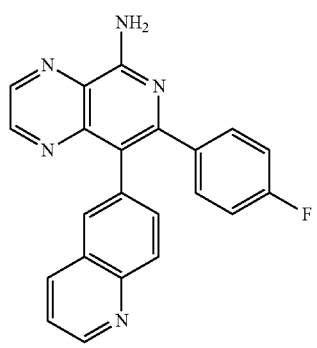 [SMILES: Nc1nc(-c2ccc(F)cc2)c(-c2ccc3ncccc3c2)c2nccnc12]
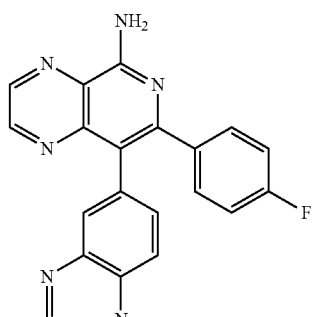
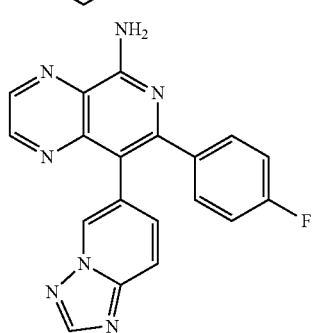
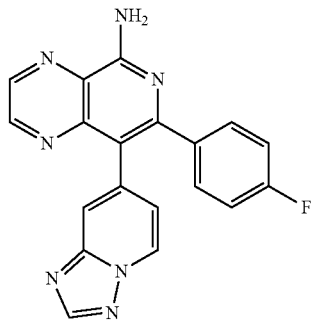 [SMILES: Nc1nc(-c2ccc(F)cc2)c(-c2ccn3ncnc3c2)c2nccnc12]
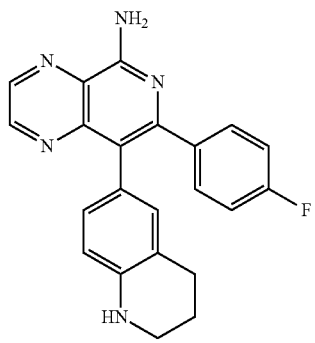 [SMILES: Nc1nc(-c2ccc(F)cc2)c(-c2ccc3c(c2)CCCN3)c2nccnc12]
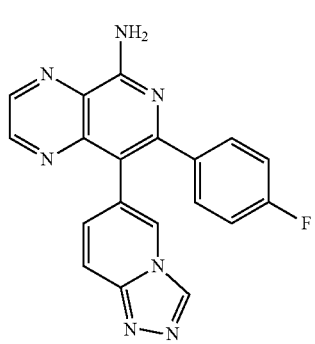

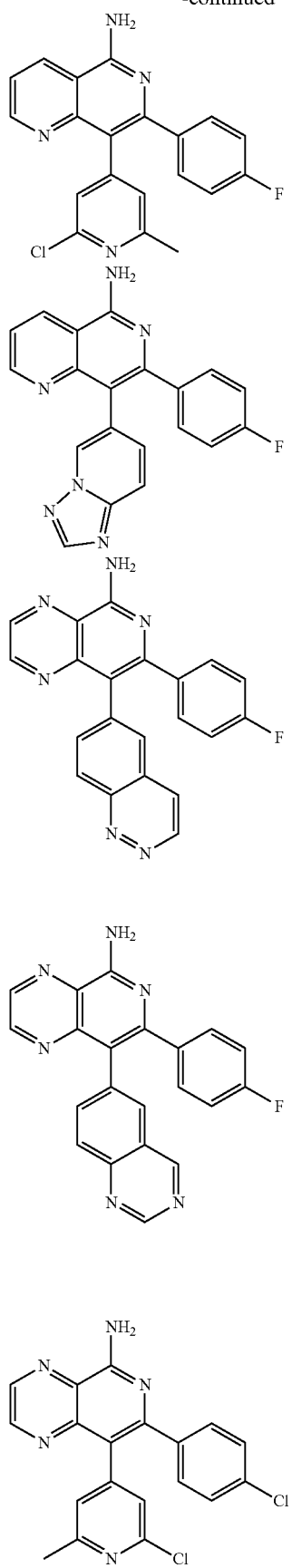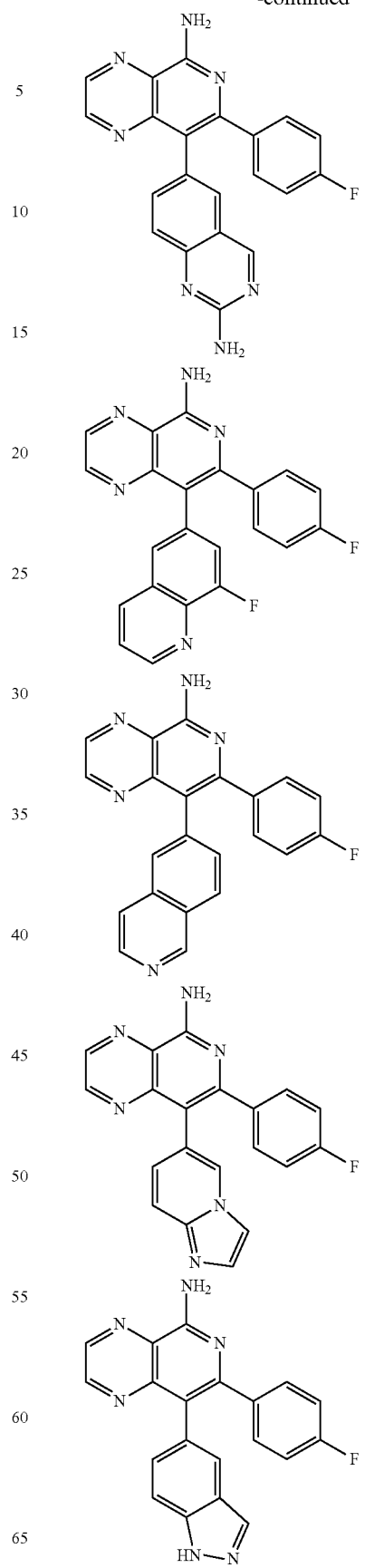

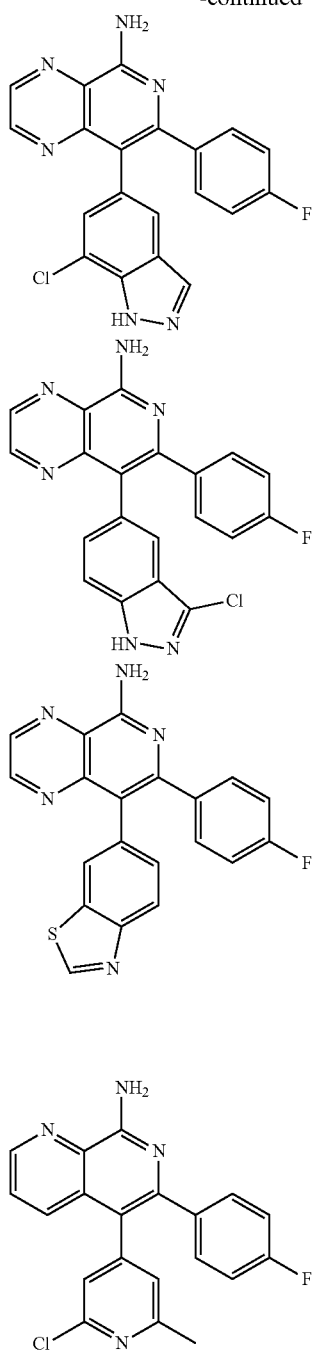
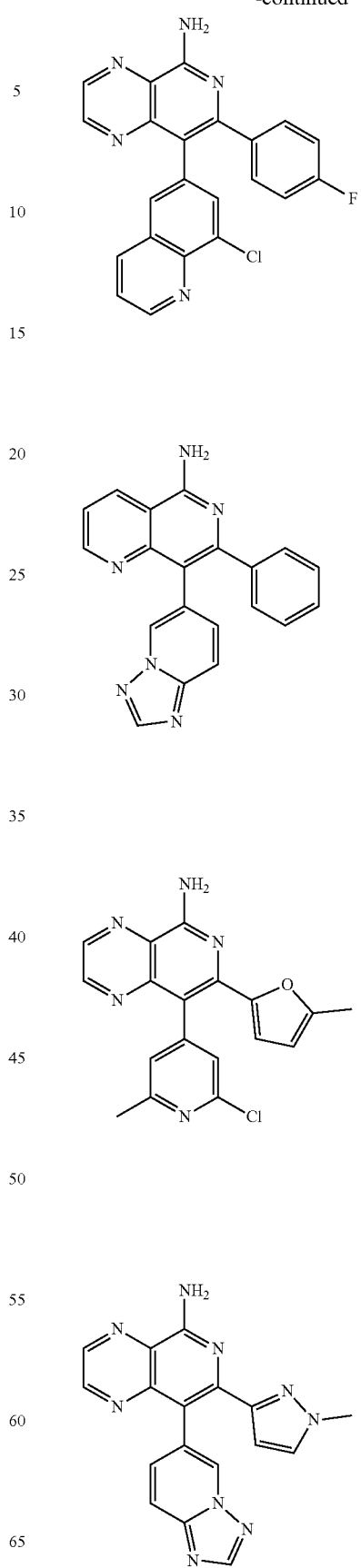

-continued

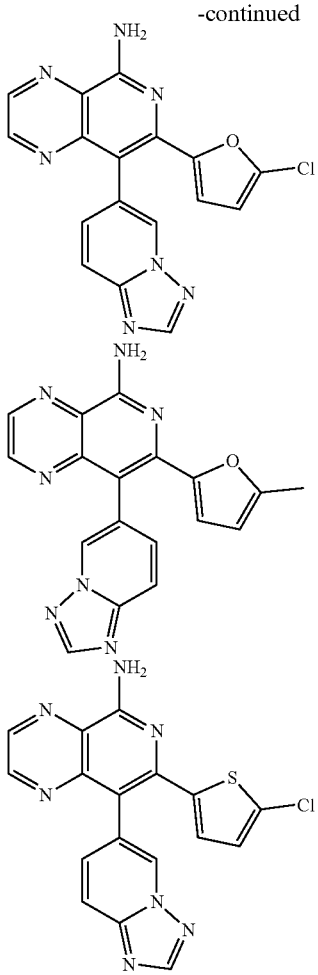

-continued

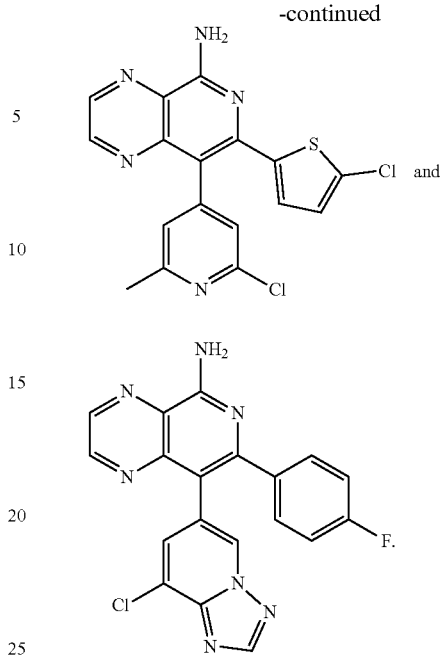

17. A method for treating a disease related to $A_{2A}$ receptor in a subject in need thereof, comprising administering a therapeutically effective amount of the compound or the pharmaceutically acceptable salt thereof according to claim 1 to the subject, wherein the disease related to $A_{2A}$ receptor is a colon cancer.

18. A pharmaceutical composition comprising the compound or the pharmaceutically acceptable salt thereof according to claim 1 and a pharmaceutical excipient.

* * * * *